United States Patent [19]

Heusler et al.

[11] 4,430,498
[45] Feb. 7, 1984

[54] 8-OXO-5-THIA-1-AZABICYCLO(4,2,0)OCT-2-ENE COMPOUNDS

[75] Inventors: Karl Heusler, Basel; Hans Bickel, Binningen; Bruno Fechtig, Reinach; Heinrich Peter, Riehen; Riccardo Scartazzini, Allschwil, all of Switzerland

[73] Assignee: Ciba-Geigy Corporation, Ardsley, N.Y.

[21] Appl. No.: 227,832

[22] Filed: Jan. 23, 1981

Related U.S. Application Data

[60] Division of Ser. No. 16,598, Mar. 1, 1979, abandoned, which is a continuation of Ser. No. 544,473, Jan. 27, 1975, abandoned, which is a continuation of Ser. No. 188,503, Oct. 12, 1971, abandoned.

[51] Int. Cl.³ .................. C07D 501/18; A61K 31/545
[52] U.S. Cl. ........................................ 544/16; 424/246
[58] Field of Search .................. 544/3, 16, 26, 27; 424/246

[56] References Cited

U.S. PATENT DOCUMENTS 3,880,833 4/1975 Scartazzini et al. ............ 260/239.1
3,883,517 5/1979 Heusler et al. ...................... 424/246

Primary Examiner—Nicholas S. Rizzo
Attorney, Agent, or Firm—Irving N. Feit

[57] ABSTRACT

The invention concerns 7-amino-ceph-3-em-4-carboxylic acid compounds of the formula

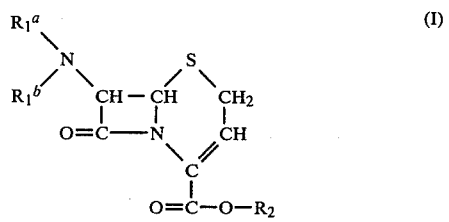

wherein $R_1^a$ represents hydrogen or an amino protective group $R_1^A$ and $R_1^b$ represent hydrogen or an acyl group Ac, or $R_1^A$ and $R_1^b$ together denote a bivalent amino protective group, and $R_2$ represents hydrogen or an organic radical $R_2^A$ which together with the —C(=O)—O— grouping forms a protected carboxyl group, or salts such compounds which possess salt-forming groups; these compounds have antibiotic properties.

4 Claims, No Drawings

8-OXO-5-THIA-1-AZABICYCLO(4,2,0)OCT-2-ENE COMPOUNDS

This is a division of application Ser. No. 016,598 filed on Mar. 1, 1979 now abandoned, which is a continuation of application Ser. No. 544,473 filed Jan. 27, 1975, now abandoned, which is a continuation of application Ser. No. 188,503 filed Oct. 12, 1971, now abandoned.

The subject of the present invention are 7-amino-8-oxo-5-thia-1-azabicyclo[4,2,0]-oct-2-ene-2-carboxylic acid compounds, especially 7-amino-ceph-3-em-4-carboxylic acid compounds of the formula

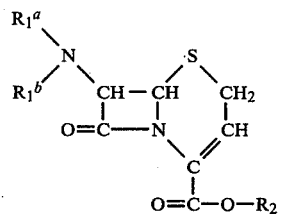

wherein $R_1{}^a$ represents hydrogen or an amino protective group $R_1{}^A$, and $R_1{}^b$ represents hydrogen or an acyl group Ac, or $R_1{}^A$ and $R_1{}^b$ together denote a bivalent amino protective group, and $R_2$ represents hydrogen or an organic radical $R_2{}^A$ which together with the —C(=O)—O— grouping forms a protected carboxyl group.

An amino protective group $R_1{}^A$ is a group which is replaceable by hydrogen, above all an acyl group Ac, and also a triarylmethyl group, especially the trityl group, as well as an organic silyl group, and also an organic stannyl group. A group Ac above all represents the acyl radical of an organic carboxylic acid or sulphonic acid, in particular the acyl radical of an optionally substituted aliphatic, cycloaliphatic, cycloaliphatic-aliphatic, aromatic, araliphatic, heterocyclic or heterocyclic-aliphatic carboxylic acid, (including formic acid), and also the acyl radical of a carbonic acid half-derivative.

A bivalent amino protective group formed by the radicals $R_1{}^A$ and $R_1{}^b$ together is, in particular, the bivalent acyl radical of an organic dicarboxylic acid, above all the diacyl radical of an aliphatic or aromatic dicarboxylic acid, and also the acyl radical of an α-aminoacetic acid which is preferably substituted in the α-position, for example, containing an aromaic or heterocyclic radical, wherein the amino group is bonded to the nitrogen atom via a methylene radical which is preferably substituted, for example containing two lower alkyl groups, such as methyl groups. The radicals $R_1{}^A$ and $R_1{}^b$ can together also represent an organic ylidene radical, such an an aliphatic, cycloaliphatic, cycloaliphatic-aliphatic or araliphatic ylidene radical.

A protected carboxyl group of the formula —C(=O)—O—$R_2{}^A$ is above all an esterified carboxyl group, but can also be an anhydride group, which is usually a mixed anhydride group.

The group $R_2{}^A$ can represent an organic radical, which together with the —C(=O)—O— grouping forms an esterified carboxyl group which can preferably be split easily; such radicals are, for example, aliphatic, cycloaliphatic, cycloaliphatic-aliphatic, aromatic or araliphatic radicals, especially optionally substituted hydrocarbon radicals of this nature, as well as heterocyclic or heterocyclic-aliphatic radicals.

The group $R_2{}^A$ can also represent an organic silyl radical, as well as an organo-metallic radical, such as an appropriate organic stannyl radical, especially a silyl or stannyl radical substituted by 1 to 3, optionally substituted, hydrocarbon radicals, such as aliphatic hydrocarbon radicals.

A radical $R_2{}^A$ which forms a preferably mixed anhydride group with the —C(=O)—O— grouping is preferably the acyl radical of an organic carboxylic acid, such as an aliphatic, cycloaliphatic, cycloaliphatic-aliphatic, aromatic or araliphatic carboxylic acid, or of a carbonic acid half-derivative, such as of a carbonic acid half-ester.

The general terms used in the preceding and following description for example have the following meanings:

An aliphatic radical, including the aliphatic radical of a corresponding organic carboxylic acid, as well as a corresponding ylidene radical, is an optionally substituted, monovalent or divalent, aliphatic hydrocarbon radical, especially lower alkyl, as well as lower alkenyl or lower alkinyl, and also lower alkylidene, which can, for example, contain up to 7, preferably up to 4, carbon atoms. Such radicals can optionally be monosubstituted, disubstituted or polysubstituted by functional groups, for example, by free, etherified or esterified hydroxyl or mercapto groups, such as lower alkoxy, lower alkenyloxy, lower alkylenedioxy, optionally substituted phenyloxy or phenyl-lower alkoxy, lower alkylthio or optionally substituted phenylthio or phenyl-lower alkylthio, lower alkoxycarbonyloxy or lower alkanoyloxy, or halogen, and also by oxo, nitro, optionally substituted amino, for example di-lower alkylamino, lower alkyleneamino, oxa-lower alkyleneamino or aza-lower alkyleneamino, as well as acylamino, such as lower alkanoylamino, optionally substituted carbamoylamino, ureidocarbonylamino or guanidinocarbonylamino, azido, acyl, such as lower alkanoyl or benzoyl, optionally functionally modified carboxyl, such as carboxyl present in the salt form, esterified carboxyl, such as lower alkoxycarbonyl, optionally substituted carbamoyl, such as N-lower alkylcarbamoyl or N,N-di-lower alkylcarbamoyl, and also optionally substituted ureidocarbonyl or guanidinocarbonyl, or nitrile, optionally functionally modified sulpho, such as sulphamoyl, or sulpho present in the salt form.

The divalent aliphatic radical of an aliphatic carboxylic acid is, for example, lower alkylene or lower alkenylene, which can optionally be monosubstituted, disubstituted or polysubstituted, for example like an aliphatic radical indicated above.

A cycloaliphatic or cycloaliphatic-aliphatic radical, including the cycloaliphatic or cycloaliphatic-aliphatic radical in a corresponding organic carboxylic acid, or a corresponding cycloaliphatic or cycloaliphatic-aliphatic ylidene radical, is an optionally substituted, monovalent or divalent, cycloaliphatic or cycloaliphatic-aliphatic, hydrocarbon radical, for example, monocyclic, bicyclic or polycyclic cycloalkyl or cycloalkenyl, also cycloalkylidene, or cycloalkyl- or cycloalkenyl-lower alkyl or cycloalkenyl-lower alkenyl, as well as cycloalkyl-lower alkylidene or cycloalkenyl-lower alkylidene, wherein cycloalkyl and cycloalkylidene for example contains up to 12, such as 3-8, preferably 3-6, ring carbon atoms, whilst cycloalkenyl for example possesses up to 12, such as 3-8, for example 5-8, preferably 5 or 6, ring carbon atoms, as well as 1 to 2 double bonds, and the aliphatic part of a cycloaliphatic-aliphatic radical can, for example, contain up to 7, preferably up to 4, carbon atoms. The above cycloaliphatic or cycloaliphatic-aliphatic radicals can, if desired, be monosubstituted, disubstituted or polysubstituted, for example by optionally substituted aliphatic hydrocarbon radicals, such as by the abovementioned, optionally substituted lower alkyl groups, or, for example like the abovementioned aliphatic hydrocarbon radicals, by functional groups.

The aromatic radical, including the aromatic radical of a corresponding carboxylic acid, is an optionally substituted aromatic hydrocarbon radical, for example a monocyclic, bicyclic or polycyclic aromatic hydrocarbon radical, in particular phenyl, as well as biphenylyl or naphthyl, which can optionally be monosubstituted, disubstituted or polysubstituted, for example like the abovementioned aliphatic and cycloaliphatic hydrocarbon radicals.

The divalent aromatic radical of an aromatic carboxylic acid is above all 1,2-arylene, especially 1,2-phenylene, which can optionally be monosubstituted, disubstituted or polysubstituted, for example like the abovementioned aliphatic and cycloaliphatic hydrocarbon radicals.

The araliphatic radical, including the araliphatic radical in a corresponding carboxylic acid, and also an araliphatic ylidene radical, is, for example, an optionally substituted araliphatic hydrocarbon radical, such as an optionally substituted aliphatic hydrocarbon radical which, for example, possesses up to three optionally substituted, monocyclic, bicyclic or polycyclic aromatic hydrocarbon radicals, and above all represents phenyl-lower alkyl or phenyl-lower alkenyl, as well as phenyl-lower alkinyl and also phenyl-lower alkylidene, and such radicals, for example, contain 1-3 phenyl groups and can optionally be monosubstituted, disubstituted or polysubstituted in the aromatic and/or aliphatic part, for example like the above-mentioned aliphatic and cycloaliphatic radicals.

Heterocyclic groups, including those in heterocyclic-aliphatic radicals, including heterocyclic or heterocyclic-aliphatic groups in corresponding carboxylic acids, are especially monocyclic, as well as bicyclic or polycyclic, azacyclic, thiacyclic, oxacyclic, thiazacyclic, thiadiazacyclic, oxazacyclic, diazacyclic, triazacyclic or tetrazacyclic radicals of aromatic character, and also corresponding partially or wholly saturated radicals, and these heterocyclic radicals can optionally be monosubstituted, disubstituted or polysubstituted, for example like the abovementioned cycloaliphatic radicals. The aliphatic part in heterocyclic-aliphatic radicals for example has the meaning given for the corresponding cycloaliphatic-aliphatic or araliphatic radicals.

The acyl radical of a carbonic acid half-derivative is preferably the acyl radical or a corresponding half-ester, wherein the organic radical of the ester group represents an optionally substituted aliphatic, cycloaliphatic, aromatic or araliphatic hydrocarbon radical or a heterocyclic-aliphatic radical, above all the acyl radical of a lower alkyl half-ester, which is optionally substituted, for example in the α-position or β-position, of carbonic acid, and of a lower alkenyl, cycloalkyl, phenyl or phenyl-lower alkyl half-ester of carbonic acid which is optionally substituted in the organic radical. Acyl radicals of a carbonic acid half-ester are, further, corresponding radicals of lower alkyl half-esters of carbonic acid, in which the lower alkyl part contains a heterocyclic group, for example one of the abovementioned heterocyclic groups of aromatic character, and both the lower alkyl radical and the heterocyclic group can optionally be substituted. The acyl radical of a carbonic acid half-derivative can also be an optionally N-substituted carbamoyl group, such as an optionally halogenated N-lower alkylcarbamoyl group.

Lower alkyl is, for example, methyl, ethyl, n-propyl, isopropyl, n-butyl, isobutyl, sec.-butyl or tert.-butyl, as well as n-pentyl, isopentyl, n-hexyl, isohexyl or n-heptyl; whilst lower alkenyl can, for example, be vinyl, allyl, isopropenyl, 2- or 3-methallyl or 3-butenyl, lower alkinyl can, for example, be propargyl or 2-butinyl, and lower alkylidene can, for example, be isopropylidene or isobutylidene.

Lower alkylene is, for example, 1,2-ethylene, 1,2-or 1,3-propylene or 1,4- butylene, whilst lower alkenylene is, for example, 1,2-ethylene or 2-buten-1,4-ylene.

Cycloalkyl is, for example, cyclopropyl, cyclobutyl, cyclopentyl, cyclohexyl or cycloheptyl, as well as adamantyl, cycloalkenyl is, for example, 2-cyclopropenyl, 1,2- or 3-cyclopentenyl, 1-, 2- or 3-cyclohexenyl, 3-cycloheptenyl or 1,4-cyclohexadienyl, and cycloalkylidene is, for example, cyclopentylidene or cyclohexylidene. Cycloalkyl-lower alkyl or cycloalkyl-lower alkenyl is, for example, cyclopropyl-, cyclopentyl-, cyclohexyl- or cycloheptyl-methyl, -1,1- or -1,2-ethyl, -1,1-, -1,2- or -1,3-propyl, -vinyl or -allyl, whilst cycloalkenyl-lower alkyl or cycloalkenyl-lower alkenyl for example represents 1-, 2- or 3-cyclopentenyl-, 1-, 2- or 3-cyclohexenyl- or 1-, 2- or 3-cycloheptenyl-methyl, -1,1- or -1,2-ethyl, -1,1-, -1,2- or -1,3-propyl, -vinyl or -allyl. Cycloalkyl-lower alkylidene is, for example, cyclohexylmethylene, and cycloalkenyl-lower alkylidene is, for example, 3-cyclohexenylmethylene.

Naphthyl is 1- or 2-naphthyl, whilst biphenylyl for example represents 4-biphenylyl.

Phenyl-lower alkyl or phenyl-lower alkenyl is, for example, benzyl, 1- or 2-phenylethyl, 1-, 2- or 3-phenylpropyl, diphenylmethyl, trityl, 1- or 2-naphthylmethyl, styryl or cinnamyl, and phenyl-lower alkylidene is, for example, benzylidene.

Heterocyclic radicals are above all optionally substituted heterocyclic radicals of aromatic character, for example appropriate monocyclic, monoazacyclic, monothiacyclic or monooxacyclic radicals, such as pyrryl, for example 2-pyrryl or 3-pyrryl, pyridyl, for example 2-, 3- or 4-pyridyl, and also pyridinium, thienyl, for example 2-or 3-thienyl, or furyl, for example 2-furyl, bicyclic monoazacyclic, monooxacyclic or monothiacyclic radicals, such as indolyl, for example 2- or 3-indolyl, quinolinyl, for example 2- or 4-quinolinyl, isoquinolinyl, for example 1-isoquinolinyl, benzofuranyl, for example 2- or 3-benzofuranyl, or benzothienyl, for example 2- or 3-benzothienyl, monocyclic diazacyclic, triazacyclic, tetrazacyclic, thiazacyclic, thiadiazacyclic or oxazacyclic radicals, such as imidazolyl, for example 2-imidazolyl, pyrimidinyl, for example 2- or 4-pyrimidinyl, triazolyl, for example 1,2,4-triazol-3-yl, tetrazolyl, for example 1- or 5-tetrazolyl, oxazolyl, for example 2-oxazolyl, isoxazolyl, for example 3-isoxazolyl, thiazolyl, for example 2-thiazolyl, isothiazolyl, for example 3-isothiazolyl or 1,2,4- or 1,3,4-thiadiazolyl, for example 1,2,4-thiadiazol-3-yl, or 1,3,4-thiadiazol-2-yl, or bicyclic diazacyclic, thiazacyclic or oxazacyclic radicals, such as benzimidazolyl, for example 2- benzimidazolyl, benzoxazolyl, for example 2-benzoxazolyl, or benzthiazolyl, for example 2-benzthiazolyl. Appropriate partially or wholly saturated radicals are, for example, tetrahydrothienyl, such as 2-tetrahydrothienyl, tetrahydrofuryl, such as 2-tetrahydrofuryl, or piperidyl, for example 2- or 4-piperidyl. Heterocyclic-aliphatic radicals are heterocyclic groups, especially those mentioned above, which contain lower alkyl or lower alkenyl. The abovementioned heterocyclyl radicals can be substituted, for example by optionally substituted aliphatic hydrocarbon radicals, especially lower alkyl, such as methyl, or, for example like the aliphatic hydrocarbon radicals, by functional groups.

Lower alkoxy is, for example, methoxy, ethoxy, n-propoxy, isopropoxy, n-butoxy, isobutoxy, sec.-butoxy, tert.-butoxy, n-pentoxy or tert.-pentoxy. These groups can be substituted, for example as in halogeno-lower alkoxy, especially 2-halogeno-lower alkoxy, for example 2,2,2-trichloroethoxy, 2-bromoethoxy or 2-iodoethoxy. Lower alkenyloxy is, for example, vinyloxy or allyloxy, lower alkylenedioxy is, for example, methylenedioxy, ethylenedioxy or isopropylidenedioxy, cycloalkoxy is, for example, cyclopentoxy, cyclohexoxy or adamantyloxy, phenyl-lower alkoxy, for example benzyloxy or 1- or 2-phenylethoxy, or heterocyclyloxy or heterocyclyl-lower alkoxy, for example pyridyl-lower alkoxy, such as 2-pyridylmethoxy, furyl-lower alkoxy, such as furfuryloxy, or thienyl-lower alkoxy, such as 2-thenyloxy.

Lower alkylthio is, for example methylthio, ethylthio or n-butylthio, lower alkenylthio is, for example allylthio, and phenyl-lower alkylthio is, for example benzylthio, whilst mercapto groups etherified by heterocyclyl radicals or heterocyclyl-aliphatic radicals are, especially, imidazolylthio, for example 2-imidazolylthio, thiazolylthio, for example 2-thiazolylthio, 1,2,4- or 1,3,4-thiadiazolylthio, for example 1,2,4-thiadiazol-3-ylthio or 1,3,4-thiadiazol-2-ylthio, or tetrazolylthio, for example 1-methyl-5-tetrazolylthio.

Esterified hydroxyl groups are, above all, halogen, for example fluorine, chlorine, bromine or iodine, as well as lower alkanoyloxy, for example acetoxy or propionyloxy.

Lower alkoxy-carbonyl is, for example, methoxycarbonyl, ethoxycarbonyl, n-propoxycarbonyl, isopropoxycarbonyl, tert.-butoxycarbonyl or tert.-pentoxycarbonyl.

N-lower alkyl-carbamoyl or N,N-di-lower alkyl-carbamoyl is, for example N-methylcarbamoyl, N-ethylcarbamoyl, N,N-dimethylcarbamoyl or N,N-diethylcarbamoyl, whilst N-lower alkylsulphamoyl for example represents N-methylsulphamoyl or N,N-dimethylsulphamoyl.

A carboxyl or sulpho group present in the alkali metal salt form is, for example, a carboxyl or sulpho group present in the sodium salt or potassium salt form.

Lower alkylamino or di-lower alkylamino is, for example, methylamino, ethylamino, dimethylamino or diethylamino, lower alkyleneamino is, for example, pyrrolidino or piperidino, oxa-lower alkyleneamino is, for example, morpholino, and aza-lower alkyleneamino is, for example, piperazino or 4-methylpiperazino. Acylamino especially represents carbamoylamino, lower alkylcarbamoylamino, such as methylcarbamoylamino, ureidocarbonylamino, guanidinocarbonylamino, lower alkanoylamino, such as acetylamino or propionylamino, and also phthalimido, or sulphoamino which is optionally present in the salt form, such as the alkali metal, for example sodium, salt form or ammonium salt form.

Lower alkanoyl is, for example, acetyl or propionyl.

Lower alkenyloxycarbonyl is, for example, vinyloxycarbonyl, whilst cycloalkoxycarbonyl and phenyl-lower alkoxycarbonyl for example represents adamantyloxycarbonyl, benzyloxycarbonyl, diphenylmethoxycarbonyl or α-4-biphenylyl-α-methylethoxycarbonyl. Lower alkoxycarbonyl, wherein lower alkyl for example contains a monocyclic, monoazacyclic, monooxacyclic, or monothiacyclic group, is, for example, furyl-lower alkoxycarbonyl, such as furfuryloxycarbonyl, or thienyl-lower alkoxycarbonyl, for example 2-thenyloxycarbonyl.

An acyl group Ac in particular represents an acyl radical of an organic carboxylic acid or of a carbonic acid half-derivative, the acyl radical being contained in a naturally occurring or biosynthetically, semi-synthetically or totally-synthetically preparable, preferably pharmacologically active, N-acyl derivative of 6-amino-penicillanic acid or 7-amino-cephalosporanic acid compounds, or represents an easily removable acyl radical, especially of a carbonic acid half-derivative.

An acyl radical Ac contained in pharmacologically active N-acyl derivatives of 6-amino-penicillanic acid or 7-aminocephalosporanic acid is, above all, a group of the formula

wherein n represents O and $R^I$ denotes hydrogen or an optionally substituted cycloaliphatic or aromatic hydrocarbon radical, or an optionally substituted heterocyclic radical, preferably of aromatic character, a functionally modified, preferably etherified hydroxyl or mercapto group or an optionally substituted amino group, or wherein n represents 1, and $R^I$ represents hydrogen or an optionally substituted, aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably possesses aromatic character and/or a quaternary nitrogen atom, or represents an optionally functionally modified, preferably etherified or esterified, hydroxyl or mercapto group, an optionally functionally modified carboxyl group, an acyl group, an optionally substituted amino group or an azido group, and each of the radicals $R^{II}$ and $R^{III}$ is hydrogen, or wherein n represents 1, $R^I$ represents an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably displays aromatic character, $R^{II}$ denotes an optionally functionally modified, preferably etherified, hydroxyl or mercapto group, an optionally substituted amino group, an optionally functionally modified carboxyl group or sulpho group, an azido group or a halogen atom, and $R^{III}$ represents hydrogen, or wherein n represents 1, each of the radicals $R^I$ and $R^{II}$ denote a functionally modified, preferably etherified or esterified, hydroxyl group, or an optionally functionally modified carboxyl group, and $R^{III}$ represents hydrogen, or wherein n represents 1, $R^I$ denotes hydrogen or an optionally substituted aliphatic, cycloaliphatic, cycloaliphatic-aliphatic, aromatic or araliphatic hydrocarbon radical, and $R^{II}$ and $R^{III}$ together represent an optionally substituted aliphatic, cycloaliphatic, cycloaliphatic-aliphatic or araliphatic hydrocarbon radical bonded to the carbon atom by a double bond, or wherein n represents 1 and $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein heterocyclic radicals preferably possess aromatic character, $R^{II}$ denotes an optionally substituted aliphatic, cycloaliphatic, cycloaliphatic-aliphatic, aromatic or araliphatic hydrocarbon radical and $R^{III}$ denotes hydrogen or an optionally substituted aliphatic, cycloaliphatic, cycloaliphatic-aliphatic, aromatic or araliphatic hydrocarbon radical.

In the abovementioned acyl groups of the formula IA, for example, n represents O and $R^I$ represents hydrogen or a cycloalkyl group with 5-7 ring carbon atoms which is optionally substituted, preferably in the 1-position by amino or by a sulphoamino group which is optionally in the salt form, for example alkali metal salt form, a phenyl, naphthyl or tetrahydronaphthyl group which is optionally substituted, preferably by hydroxyl, lower alkoxy, for example methoxy, and/or halogen, for example chlorine, a heterocyclic group such as a 4-isoxazolyl group which is optionally substituted, for example by lower alkyl, e.g. methyl, and/or phenyl, which can in turn carry substituents, such as halogen, for example chlorine, or an amino group which is preferably N-substituted, for example by an optionally substituted lower alkyl radical, such as a lower alkyl radical containing halogen, for example chlorine, or n represents 1 and $R^I$ represents a lower alkyl group which is optionally substituted, preferably by halogen, e.g. chlorine, by phenyloxy which in turn may optionally contain hydroxy and/or halogen, such as chlorine, by amino and/or by carboxyl, furthermore a lower alkenyl group, a phenyl group which is optionally substituted, for example, by hydroxyl, halogen, for example chlorine and/or optionally substituted phenyloxy, a pyridyl, pyridinium, thienyl, 1-imidazolyl or 1-tetrazolyl group which is optionally substituted, for example by amino or aminomethyl, an optionally substituted lower alkoxy group, a phenyloxy group which is optionally substituted, for example by hydroxy and/or halogen, such as chlorine, a lower alkylthio or lower alkenylthio group, an optionally substituted, for example lower alkylsubstituted, such as methyl-substituted, phenylthio, 2-imidazolylthio, 1,2,4-triazol-3-ylthio, 1,3,4-triazol-2-ylthio, 1,2,4-thiadiazol-3-ylthio, such as 5-methyl-1,2,4-thiadiazol-3-ylthio, 1,3,4-thiadiazol-2-ylthio, such as 5-methyl-1,3,4-thiadiazol-2-ylthio, or 5-tetrazolylthio such as 1-methyl-5-tetrazolylthio group, a halogen atom, especially chlorine or bromine atom, an optionally functionally modified carboxyl group, such as lower alkoxycarbonyl, cyano, or carbamoyl which is optionally N-substituted, for example by phenyl, an optionally substituted lower alkanoyl or benzoyl group, or an azido group, and $R^{II}$ and $R^{III}$ represent hydrogen, or n represents 1, $R^I$ represents a phenyl or thienyl group which is optionally substituted, for example by hydroxyl and/or halogen, for example chlorine and also represents a 1,4-cyclohexadienyl group, $R^{II}$ represents an optionally substituted amino group, for example optionally substituted carbamoylamino group, such as guanidinocarbonylamino, or a sulphoamino group optionally present in salt form, for example, in the alkali metal salt form, an azido group, a carboxyl group optionally present in salt form, for example, in the alkali metal salt form, or in the esterified form, e.g. in the form of lower alkoxy-carbonyl, a cyano group, a sulpho group, an optionally substituted lower alkoxy or phenyloxy group, or a halogen e.g. chlorine or bromine atom, and $R^{III}$ represents hydrogen, or n represents 1, $R^I$ and $R^{II}$ each represent halogen, for example bromine, or lower alkoxycarbonyl, for example methoxycarbonyl, and $R^{III}$ represents hydrogen, or n represents 1, and each of the groups $R^I$, $R^{II}$ and $R^{III}$ represent lower alkyl, for example methyl.

Such acyl radicals Ac are, for example, formyl, cyclopentylcarbonyl, α-aminocyclopentylcarbonyl or α-aminocyclohexylcarbonyl (with an optionally substituted amino group, for example a sulphoamino group optionally present in the salt form, or an amino group substituted by an acyl radical which can preferably be split off easily, for example on treatment with an acid agent, such as trifluoroacetic acid, or with a chemical reducing agent, such as zinc in the presence of aqueous acetic acid, or by an acyl radical which can be converted into such a radical, preferably a suitable acyl radical of a carbonic acid half-ester, such as 2,2,2-trichloroethoxycarbonyl, 2-bromoethoxycarbonyl, 2-iodoethoxycarbonyl, tert.-butoxycarbonyl or phenacyloxycarbonyl, or of a carbonic acid half-amide, such as carbamoyl or N-methylcarbamoyl) or by trityl, 2,6-dimethoxybenzoyl, tetrahydronaphthoyl, 2-methoxynaphthoyl, 2-ethoxy-naphthoyl, benzyloxycarbonyl, hexahydrobenzyloxycarbonyl, 5-methyl-3-phenyl-4-isoxazolylcarbonyl, 3-(2-chlorophenyl)-5-methyl-4-isoxazolylcarbonyl, 3-(2,6-dichlorophenyl)-5-methyl-4-isoxazolylcarbonyl, 2-chloroethylaminocarbonyl, acetyl, propionyl, butyryl, hexanoyl, octanoyl, acrylyl, crotonoyl, 3-butenoyl, 2-pentenoyl, methoxyacetyl, methylthioacetyl, butylthioacetyl, allylthioacetyl, chloroacetyl, bromoacetyl, dibromoacetyl, 3-chloropropionyl, 3-bromopropionyl, aminoacetyl or 5-amino-5-carboxylvaleryl (with an amino group which is optionally substituted, for example as indicated, and/or a carboxyl group which is optionally functionally modified and is, for example, in the salt form, such as the sodium salt form, or in the ester form, such as in the lower alkyl ester, for example methyl or ethyl ester form), azidoacetyl, carboxyacetyl, methoxycarbonylacetyl, ethoxycarbonylacetyl, bis-methoxycarbonylacetyl, N-phenylcarbamoylacetyl, cyanoacetyl, α-cyanopropionyl, 2-cyano-3,3-dimethylacrylyl, phenylacetyl, α-bromophenylacetyl, α-azidophenylacetyl, 3-chlorophenylacetyl, 4-aminomethylphenylacetyl (with an amino group which is optionally substituted, for example as indicated), phenacylcarbonyl, phenyloxyacetyl, 4-trifluoromethylphenyloxyacetyl, benzyloxyacetyl, phenylthioacetyl, bromophenylthioacetyl, 2-phenyloxypropionyl, α-phenyloxyphenylacetyl, α-methoxyphenylacetyl, α-ethoxyphenylacetyl, α-methoxy-3,4-dichlorophenylacetyl, α-cyanophenylacetyl, particularly phenylglycyl, 4-hydroxyphenylglycyl, 3-chloro-4-hydroxyphenylglycyl, or 3,5-dichloro-4-hydroxyphenylglycyl in which residues the amino group may optionally be substituted, for example as indicated above), furthermore benzylthioacetyl, benzylthiopropionyl, α-carboxyphenylacetyl (with a carboxyl group which is optionally functionally modified, for example as indicated above), 3-phenylpropionyl, 3-(3-cyanophenyl)propionyl, 4-(3-methoxyphenyl)-butyryl, 2-pyridylacetyl, 4-aminopyridiniumacetyl (optionally with an amino group which is substituted, for example as indicated above), 2-thienylacetyl, 2-tetrahydrothienylacetyl, α-carboxy-2-thienylacetyl or α-carboxy-3-thienylacetyl (optionally with a carboxyl group which is functionally modified, for example as indicated above), α-cyano-2-thienylacetyl, α-amino-2-thienylacetyl or α-amino-3-thienylacetyl (optionally with an amino group which is substituted, for example as indicated above), α-sulphophenylacetyl (optionally with a sulpho group which is functionally modified, for example like the carboxyl group) 3-thienylacetyl, 2-furylacetyl, 1-amidazolylacetyl, 1-tetrazolylacetyl, 3-methyl-2-imidazolylthioacetyl, 1,2,4-triazol-3-ylthio-acetyl, 1,3,4-triazol-2-ylthioacetyl, 5-methyl-1,2,4-thiadiazol-3-ylthioacetyl, 5-methyl-1,3,4-thiadiazol-2-ylthioacetyl or 1-methyl-5-tetrazolylthioacetyl, An easily removable acyl radical Ac, especially of a carbonic acid half-ester, is above all an acyl radical of a half-ester of carbonic acid which can be split off by reduction, for example by treatment with a chemical reducing agent, or by treatment with acid, for example with trifluoroacetic acid, such as a lower alkoxycarbonyl radical which preferably shows multiple branching in the α-position or is substituted by acylcarbonyl, especially benzoyl radicals, or substituted by halogen atoms in the α-position, for example tert.-butoxycarbonyl, tert.-pentoxycarbonyl, phenacyloxycarbonyl, 2,2,2-trichloroethoxycarbonyl or 2-iodoethoxycarbonyl or a radical which can be converted into the latter, such as 2-chloroethoxycarbonyl or 2-bromoethoxycarbonyl, and also preferably polycyclic cycloalkoxycarbonyl, for example adamantyloxycarbonyl, optionally substituted phenyl-lower alkoxycarbonyl, above all α-phenyl-lower alkoxycarbonyl, wherein the α-position preferably has several substituents, for example diphenylmethoxycarbonyl or α-4-biphenylyl-α-methylethoxycarbonyl, or furyl-lower alkoxycarbonyl, above all α-furyl-lower alkoxycarbonyl, for example furfuryloxycarbonyl.

A divalent acyl group formed by the two radicals $R_1^A$ and $R_1^b$ is, for example, the acyl radical of a lower alkanedicarboxylic acid or lower alkenedicarboxylic acid, such as succinyl, or of an o-aryldicarboxylic acid, such as phthaloyl.

A further divalent radical formed by the groups $R_1^A$ and $R_1^b$ is, for example, a 1-oxo-3-aza-1,4-butylene radical which, especially in the 2-position, contains, for example, optionally substituted phenyl or thienyl, and is optionally substituted in 4-position by one or preferably two lower alkyl residues, for example 4,4-dimethyl-2-phenyl-1-oxo-3-aza-1,4-butylene.

An organic radical $R_2^A$ which together with the —C(=O)—O— grouping forms an esterified carboxyl group which can preferably be split easily, for example represents a 2-halogeno-lower alkyl radical $R_2^a$, wherein halogen has an atomic weight of above 19. Such a radical together with the —C(=O)—O— grouping forms an esterified carboxyl group which can easily be split on treatment with chemical reducing agents under neutral or weakly acid conditions, for example with zinc in the presence of aqueous acetic acid, or forms an esterified carboxyl group which can easily be converted into such a carboxyl group, and is, for example, 2,2,2-trichloroethyl, 2-chloroethyl, 2-bromoethyl or 2-iodoethyl.

A further group $R_2^A$, which together with the —C(=O)—O— grouping represents an esterified carboxyl group which can also be split easily on treatment with chemical reducing agents under neutral or weakly acid conditions, for example on treatment with zinc in the presence of aqueous acetic acid, is an arylcarbonylmethyl group $R_2^b$, wherein aryl especially represents an optionally substituted phenyl group, and preferably phenacyl.

The group $R_2^A$ can also represent the radical $R_2^c$, which denotes an arylmethyl group, wherein aryl especially denotes a monocyclic, preferably substituted, aromatic hydrocarbon radical. Such a radical together with the —C(=O)—O— grouping forms an esterified carboxyl group which can easily be split on irradiation, preferably with ultraviolet light, under neutral or acid conditions. Such an aryl radical contains, as substituents, especially lower alkoxy, for example methoxy (which in the case of the preferred phenyl radical are above all in the 3-, 4- and/or 5-position), and/or above all nitro (in the case of the preferred phenyl radical, preferably in the 2-position). Such radicals $R_2^c$ are, above all, 3- or 4-methoxybenzyl, 3,5-dimethoxybenzyl, 2-nitrobenzyl or 4,5-dimethoxy-2-nitrobenzyl.

A group $R_2^A$ can also represent the radical $R_2^d$, which together with the —C(=O)—O— grouping forms an esterified carboxyl group which can easily be split under acid conditions, for example on treatment with trifluoroacetic acid or formic acid. Such a radical $R_2^d$ is above all a methyl group, which is polysubstituted by optionally substituted hydrocarbon radicals, or is monosubstituted by a carbocyclic aryl group possessing electron-donating substituents or by a heterocyclic group or aromatic character possessing oxygen or sulphur atoms as a ring member, or $R_2^d$ denotes a ring member in a polycycloaliphatic hydrocarbon radical, or denotes the ring member which is in the α-position to the oxygen atom or sulphur atom in an oxacycloaliphatic or thiacycloaliphatic radical.

Preferred polysubstituted methyl groups $R_2^d$ are, for example, tert.-butyl, tert.-pentyl, benzhydryl, 4,4'-dimethoxy-benzhydryl or 2-(4-biphenylyl)-2-propyl, whilst a methyl group $R_2^d$ containing the abovementioned substituted aryl group or the heterocyclic group is, for example, 4-methoxybenzyl or 3,4-dimethoxy-benzyl, or 2-furyl. A polycycloaliphatic hydrocarbon radical in which the methyl group $R_2^d$ represents a preferably triply branched ring member is, for example, adamantyl, such as 1-adamantyl, and an abovementioned oxacycloaliphatic or thiacycloaliphatic radical $R_2^d$ is a 2-tetrahydrofuryl, 2-tetrahydropyranyl or 2,3-dihydro-2-pyranyl or corresponding sulphur analogues.

The radical $R_2^A$ can also represent a radical $R_2^e$, which together with the —C(=O)—O— grouping forms an esterified carboxyl group which can be split hydrolytically, for example under weakly basic or under acid conditions. Such a radical $R_2^e$ is preferably a radical which together with the —C(=O)—O— grouping forms an activated ester, such as nitrophenyl, for example 4-nitrophenyl or 2,4-dinitrophenyl, nitrophenyl-lower alkyl, for example 4-nitrobenzyl, polyhalogenophenyl, for example 2,4,6-trichlorophenyl or 2,3,4,5,6-pentachlorophenyl, and also cyanomethyl, as well as acylaminomethyl, for example phthaliminomethyl or succinyliminomethyl, furthermore trityl or bis-aryloxymethyl, e.g. bis-(4-methoxyphenyloxy)-methyl.

The group $R_2^A$ can also represent a radical $R_2^f$ which together with the carboxyl grouping —C(=O)—O— forms an esterified carboxyl group which can be split under hydrogenolytic conditions, and is, for example, an optionally substituted α-aryl-lower alkyl radical, such as benzyl, 4-methoxy-benzyl, 4-nitrobenzyl, benzhydryl or 4,4-dimethoxybenzhydryl.

The group $R_2^A$ can also represent a radical $R_R^g$ which together with the carboxyl grouping —C(=O)—O— forms an esterified carboxyl group which can be split under physiological conditions, above all lower alkanoyloxymethyl, for example acetoxymethyl or pivaloyloxymethyl.

A silyl radical or stannyl radical $R_2^A$ preferably contains optionally substituted aliphatic, cycloaliphatic, aromatic or araliphatic hydrocarbon radicals, such as lower alkyl, cycloalkyl, phenyl or phenyl-lower alkyl groups, and above all represents tri-lower alkylsilyl, for example trimethylsilyl, or tri-lower alkylstannyl, for example tri-n-butylstannyl.

An acyl radical which together with the —C(=O)—O— grouping forms a mixed anhydride group which can be split, preferably hydrolytically, is, for example, the acyl radical of one of the abovementioned organic carboxylic acids or carbonic acid half-derivatives, such as lower alkanoyl, for example acetyl, or lower alkoxycarbonyl, for example, ethoxycarbonyl.

Salts are, in particular, those of the compounds of the formula I in which $R_2$ represents hydrogen, and are above all metal salts or ammonium salts, such as alkali metal salts and alkaline earth metal salts, for example sodium, potassium, magnesium or calcium salts, as well as ammonium salts with ammonia or suitable organic amines, for which, above all, aliphatic, cycloaliphatic, cycloaliphaticaliphatic and araliphatic primary, secondary or tertiary monoamines, diamines or polyamines, as well as heterocyclic bases can be used to form salts, such amines being lower alkylamines, for example triethylamine, hydroxy-lower alkylamines, for example 2-hydroxyethylamine, bis-(2-hydroxyethyl)amine or tri-(2-hydroxyethyl)-amine, basic aliphatic esters of carboxylic acids, for example 4-aminobenzoic acid-2-diethylamino-ethyl ester, lower alkyleneamines, for example 1-ethylpiperidine, cycloalkylamines, for example bicyclohexylamine, or benzylamines, for example N,N'-dibenzylethylenediamine, and also bases of the pyridine type, for example pyridine, collidine or quinoline. Compounds of the formula I, in which, for example, $R_1^a$ and $R_1^b$ represent hydrogen or which possess a basic group in a radical $R_1^a$ or $R_1^b$, can also form acid addition salts, for example with inorganic acids, such as hydrochloric acid, sulphuric acid or phosphoric acid, or with suitable organic carboxylic acids or sulphonic acids, for example trifluoroacetic acid. Compounds of the formula I, wherein $R_2$ represents hydrogen, and in which $R_1^a$ and $R_1^b$ denote hydrogen, or which contain a basic group in a radical $R_1^a$ and $R_1^b$, can also be present in the form of an internal salt, that is to say in the form of the zwitter ion.

The compound of the formula I display valuable pharmacological properties or can be used as intermediate products for the manufacture of compounds showing such properties. Compounds of the formula I, wherein $R_1^a$ represents an acyl radical Ac occurring in pharmacologically active N-acyl derivatives of 6-amino-penam-3-carboxylic acid compounds or 7-amino-ceph-3-em-4-carboxylic acid compounds, and $R_1^b$ represents hydrogen, and $R_2$ denotes hydrogen or an organic radical $R_2^A$ which can easily be split off under physiological conditions, are active againt micro-organisms, such as Gram-positive bacteria, for example against *Staphylococcus aureus* (e.g. in mice in doses from about 0.0001 to about 0.02 g/kg p.o., especially from about 0.001 to about 0.01 g/kg p.o.) and Gram-negative bacteria, for example against *Escherichia coli* (e.g. in mice in doses from about 0.001 to about 0.05 g/kg p.o., especially from about 0.005 to about 0.04 g/kg p.o.), and especially also against penicillin-resistant bacteria. The new compounds are therefore useful accordingly, for example, in the form of antibiotically active preparations.

Compounds of the formula I, wherein the radicals $R_1^a$ and $R_1^b$ represent hydrogen or wherein $R_1^a$ denotes an amino protective group different from the abovementioned acyl radical, and $R_1^b$ represents hydrogen, or wherein $R_1^A$ and $R_1^b$ together represent a divalent amino protective group and $R_2$ represents hydrogen, or wherein $R_1^a$ and $R_1^b$ have the abovementioned meanings, and $R_2$ represents an organic radical $R_2^A$ which together with the —C(=O)—O— grouping forms an esterified carboxyl group which can preferably be split easily, are valuable intermediate products, which can be converted into the above mentioned pharmacologically active compounds in a simple manner, for example as described below.

Particularly valuable compounds are those of the formula I, wherein $R_1^a$ denotes hydrogen or an acyl radical contained in a fermentatively (i.e., a naturally occurring) or biosynthetically, semi-synthetically or totally-synthetically preparable, especially pharmacologically active, such as highly active, N-acyl derivative of a 6-amino-penicillanic acid compound or 7-aminocephalospora Ac acid compound, or denotes an easily removable acyl radical of a carbonic acid half-derivative, especially of a carbonic acid half-ester, $R_1^b$ represents hydrogen and $R_2$ represents hydrogen or an organic radical $R_2^A$, which together with the —C(=O)—O— grouping forms an esterified carboxyl group which can easily be split on treatment with water, with an acid agent, with a chemical reducing agent under neutral or weakly acid conditions, hydrolytically or hydrogenolytically, or under physiological conditions, or forms an esterified carboxyl group which can be converted into the above carboxyl group, and, for example, represents trimethylsilyl, tert.-butyl, diphenylmethyl, 2,2,2-trichloroethyl, 2-chloroethyl, 2-bromoethyl, 2-iodoethyl, phenacyl, 4-methoxybenzyl, diphenylmethyl, 4,4'-dimethoxy-diphenylmethyl, 4-nitrobenzyl, trityl, bis-(4-methoxyphenyloxy)-methyl or acetonyl, and also salts of such compounds which have salt-forming groups.

Above all, $R_1^a$ in a compound of the formula I represents hydrogen or an acyl radical contained in fermentatively (i.e. naturally occurring) or biosynthetically preparable N-acyl derivatives of 6-amino-penam-3-carboxylic acid compounds or 7-amino-ceph-3-em-4-carboxylic acid compounds, such as an optionally substituted phenylacetyl or phenyloxyacetyl radical, and also an optionally substituted lower alkanoyl or lower alkenoyl radical, for example 4-hydroxy-phenylacetyl, hexanoyl, octanoyl, 3-hexenoyl, 5-amino-5-carboxy-valeryl, n-butylmercaptoacetyl or allylmercaptoacetyl, and especially phenylacetyl or phenyloxyacetyl, an acyl radical occurring in highly active N-acyl derivatives of 6-amino-penam-3-carboxylic acid compounds or 7-amino-ceph-3-em-4-carboxylic acid compounds, such as formyl, 2-chloroethylcarbamoyl; cyanoacetyl or 2-thienylacetyl, especially phenylglycyl; wherein phenyl represents optionally hydroxyl-substituted and/or halogen-substituted, for example chlorine-substituted phenyl, e.g. phenyl or 3- or 4-hydroxy-, 3-chloro-4- hydroxy- or 3,5-dichloro-4-hydroxy-phenyl, and wherein the amino group is optionally substituted and, e.g. represents a sulphoamino group, optionally present in the salt form, or an amino group which is substituted by a hydrolytically cleavable trityl group or an optionally substituted carbamoyl group, such as an optionally substituted ureidocarbonyl group, for example ureidocarbonyl or $N^3$-trichloromethylureidocarbonyl, or by an optionally substituted guanidinocarbonyl group, e.g., guanidinocarbonyl, or by an acyl radical which can be split off, preferably easily, for example on treatment with an acid agent, such as trifluoroacetic acid, or with a chemical reducing agent, such as zinc in the presence of aqueous acetic acid, or an acyl radical which can be converted into such an acyl radical, preferably a suitable acyl radical of a carbonic acid half-ester, such as 2,2,2-trichloroethyloxycarbonyl, 2-chloroethoxycarbonyl, 2-bromoethoxycarbonyl, 2-iodoethoxycarbonyl, tert.-butoxycarbonyl or phenacyloxycarbonyl, or of a carbonic acid half-amide, such as carbamoyl or N-methylcarbamoyl, or in which the amino group is connected to the nitrogen atom of the 7-amino group by a methylene group optionally substituted by lower alkyl, e.g. two methyl groups, also thienylglycyl, such as 2-thienylglycyl (optionally with an amino group which is substituted, e.g. as indicated above), or 1-aminocyclohexylcarbonyl (optionally with an amino group which is substituted, e.g. as indicated above) and also α-carboxyphenylacetyl or α-carboxy-2-thienylacetyl (optionally with a functionally modified carboxyl group, e.g. a carboxyl group present in the salt form, such as sodium salt form, or in the ester form, such as the lower alkyl, e.g. methyl, or phenyl-lower alkyl, e.g. diphenylmethyl, ester form) or α-sulpho-phenylacetyl (optionally with a sulpho group which is functionally modified, for example like the carboxyl group) or an acyl radical of a carbonic acid half-ester which can be split off easily, especially under acid conditions, for example on treatment with trifluoroacetic acid or reductively, for example with zinc in the presence of aqueous acetic acid, such as tert.-butoxycarbonyl, phenyl-carbonyl, 2,2,2-trichloroethoxycarbonyl or 2-iodoethoxy-carbonyl, or 2-bromoethoxycarbonyl, which can be converted into the latter, and $R_1^b$ represents hydrogen and $R_2$ represents hydrogen or a radical $R_2^A$, which together with the —C(=O)—O— grouping forms an esterified carboxyl group which can be split easily on treatment with a chemical reducing agent under neutral or weakly acid conditions, with an acid agent, or hydrolytically, preferably under weakly basic conditions, furthermore hydrogenolytically or under physiological conditions, and above all represents methyl which is polysubstituted by optionally substituted hydrocarbon radicals, such as lower alkyl radicals, especially tert.butyl or diphenylmethyl, and 2,2,2-trichloroethyl, 2-iodoethyl, or 2-chloroethyl or 2-bromoethyl which can easily be converted into 2-iodoethyl, or phenacyl, as well as 4-methoxybenzyl or 4-nitrobenzyl and also diphenylmethyl, 4,4'-dimethoxy-diphenylmethyl, trityl or bis-(4-methoxyphenyloxy)-methyl, as well as acetyloxymethyl or pivaloyloxymethyl.

The invention above all relates to compounds of the formula

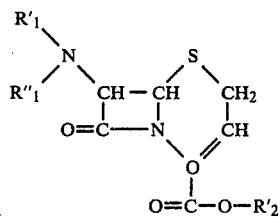

wherein $R_1'$ represents hydrogen, and $R_1''$ is hydrogen, or an acyl group of the formula

wherein Ar represents phenyl, 3- or 4-hydroxyphenyl, 3-chloro-4-hydroxy-phenyl, 3,5-dichloro-4-hydroxy-phenyl or 2-thienyl, and R represents hydrogen or optionally protected amino, carboxyl or sulfo, such as acylamino, e.g. tert.butoxy-carbonylamino, 2,2,2-trichloroethoxycarbonylamino, 2-iodoethoxycarbonylamino, 2-bromoethoxycarbonylamino or 2-guanylureido, furthermore sulphoamino or tritylamino, or esterified carboxyl, such as diphenylmethoxycarbonyl, or in which $R_1''$ is the acyl group of the formula I b, in which Ar has the meaning given above and R is an amino group which is joined to $R_1'$ representing methylene or isopropylene, and $R_2'$ represents hydrogen, tert.butyl, 2,2,2-trichloroethyl, 2-iodoethyl, 2-bromoethyl, phenacyl, 4-nitrobenzyl or 4-methoxybenzyl, and also diphenylmethyl, 4,4'-dimethoxy-diphenylmethyl, trityl or bis-(4-methoxyphenyloxy)-methyl, or salts of such compounds.

The new compounds of the present invention are obtained in a suprising manner if, in a 4β-(2-hydroxyethylthio)-1-(α-phosphoranylidene-protected carboxymethyl)-3β-N-$R_1^A$-N-$R_1^b$-amino-azetidin-2-one compound of the formula

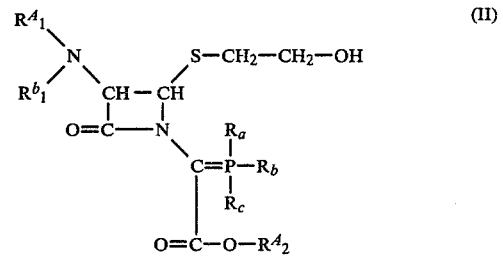

wherein each of the radicals $R_a$, $R_b$ and $R_c$ represents an optionally substituted hydrocarbon radical, the carbinol group is oxidised to a formyl group and, if desired, in a compound obtainable the group $R_1^A$ and/or the radical $R_1^b$ representing an acyl group Ac, or a divalent amino protective group formed by $R_1^A$ and $R_1^b$, is split off, and, if desired, the free amino group in a compound thus obtainable is protected, and/or, if desired, a protected carboxyl group of the formula —C(=O)—O—$R_2^A$ in a compound obtained is converted into the free carboxyl group or into a different protected carboxyl group of the formula —C(=O)—O—$R_2^A$, and, if desired, a free carboxyl group in a compound obtained is converted into a protected carboxyl group of the formula —C(-

=O)—O—$R_2^A$, and/or, if desired, a compound obtained is converted into another compound of the formula I, and/or, if desired, a compound obtained having a salt-forming group is converted into a salt or a salt obtained is converted into the free compound or into another salt, and/or, if desired, an isomer mixture obtained is separated into the individual isomers.

In the starting material of the formula II, each of the groups $R_a$, $R_b$, and $R_c$ above all denote a lower alkyl radical which is optionally substituted by functional groups, for example by optionally etherified or esterified hydroxyl groups, such as lower alkoxy group and/or halogen atoms, or denote a phenyl radical which is optionally substituted, for example by aliphatic hydrocarbon radicals, such as lower alkyl groups, and/or by the functional groups, such as optionally etherified or esterified hydroxyl groups, such as lower alkoxy groups or halogen atoms, or nitro groups.

The oxidation of a compound of the formula II can, surprisingly, be effected by treatment with an oxidising organic sulphoxide compound in the presence of agents possessing dehydrating or water-absorbent properties. Oxidising sulphoxide compounds are, above all, aliphatic sulphoxide compounds, such as di-lower alkylsulphoxides, above all dimethylsulphoxide, or lower alkylenesulphoxides, for example tetramethylenesulphoxide. As agents possessing dehydrating or water-absorbing properties, there should above all be mentioned acid anhydrides, especially anhydrides of organic carboxylic acids, such as aliphatic or aromatic carboxylic acids, for example, anhydrides of lower alkanecarboxylic acids, especially acetic anhydride, and also propionic anhydride, or benzoic anhydride, as well as anhydrides or inorganic acids, especially of phosphoric acids, such as phosphorus pentoxide. The above anhydrides, above all of organic carboxylic acids, for example acetic anhydride, are preferably used in an approximately 1:1 mixture with the sulphoxide oxidising agent. Further dehydrating or water-absorbing agents are carbodiimides, above all dicyclohexylcarbodiimide, as well as diisopropylcarbodiimide, or keteneimines, for example diphenyl-N-p-tolylketeneimine; these reagents are preferably used in the presence of acid catalysts, such as phosphoric acid or pyridinium trifluoroacetate or pyridinium phosphate. Sulphur trioxide can also be used as a dehydrating or water-absorbing agent, in which case it is customarily in the form of a complex, for example with pyridine.

The sulphoxide oxidising agent is usually employed in excess. Sulphoxide compounds which are liquid under the reaction conditions, especially dimethylsulphoxide, can, for example, simultaneously serve as the solvent; inert diluents, such as optionally halogenated hydrocarbons, preferably of aliphatic or aromatic character, for example benzene, or mixtures of solvents, can additionally be used as solvents.

The above oxidation reaction is carried out with cooling, if desired, but is in most cases carried out at room temperature or slightly elevated temperature, for example at temperatures of about −20° C. to about 100° C.

In the reaction, a carbonyl compound formed as an intermediate product according to the process, and having the formula

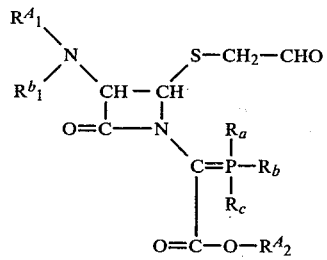

(IIa)

is cyclised directly under the reaction conditions, and without being isolated, to give the desired 7-aminoceph-3-em-4-carboxylic acid compound of the formula I.

In the process according to the invention it is possible, where necessary, to protect temporarily, in a manner which is in itself known, free functional groups in the starting substances which do not participate in the reaction, for example free hydroxyl, mercapto and amino groups, for example by acylation, tritylation or silylation, and free carboxyl groups for example by esterification, including silylation, and to liberate these groups, if desired, in each case after the reaction has taken place, in a manner which is in itself known.

In a resulting compound, an amino protective group $R_1^A$ or $R_1^b$, especially an easily removable acyl group, can be removed in a manner which is in itself known, for example a tert.-butoxycarbonyl group by treatment with trifluoroacetic acid and a 2,2,2-trichloroethoxycarbonyl, 2-iodoethoxycarbonyl or phenacyloxycarbonyl group by treatment with a suitable metal or a metal compound, for example zinc, or with a chromium-II compound, such as chromium-II chloride or acetate, advantageously in the presence of a hydrogen-donating agent which together with the metal or the metal compound generates nascent hydrogen, preferably in the presence of aqueous acetic acid. It is furthermore possible in a resulting compound of the formula I, wherein a carboxyl group —C(=O)—O—$R_2$ preferably represents a carboxyl group which is protected, for example by esterification, including a silylation or stannylation, for example by reaction with a suitable organic halogenosilicium or halogenotin-IV compound, such as trimethylchlorosilane or tri-n-butyltin chloride, to remove a suitable acyl group $R_1^A$ or $R_1^b$, wherein free functional groups which may be present are optionally protected, by treatment with an imide-halide-forming agent, reaction of the resulting imide-halide with an alcohol and splitting of the imino-ether formed, whereby a carboxyl group protected, for example, by an organic silyl radical can already be liberated in the course of the reaction.

Imide-halide-forming agents, in which halogen is bonded to an electrophilic central atom, are above all acid halides, such as acid bromides and especially acid chlorides. These are, above all, acid halides of inorganic acids, above all of phosphorus-containing acids, such as phosphorus oxyhalides, phosphorus trihalides and especially phosphorus pentahalides, for example, phosphorus oxychloride, phosphorus trichloride and above all phosphorus pentachloride, as well as pyrocatechylphosphorus trichloride, as well as acid halides, especially chlorides, of sulphur-containing acids or of carboxylic acids, such as thionyl chloride, phosgene or oxalyl chloride.

The reaction with one of the imide-halide-forming agents mentioned is preferably carried out in the presence of a suitable base, especially an organic base, above all a tertiary amine, for example a tertiary aliphatic monoamine or diamine, such as a tri-lower alkylamine, for example trimethylamine, triethylamine or ethyldiisopropylamine, or of an N,N,N',N'-tetra-lower alkyl-lower alkylenediamine, for example N,N,N',N'-tetramethyl-1,5-pentylene-diamine or N,N,N',N'-tetramethyl-1,6-hexylenediamine, a monocyclic or bicyclic monoamine or diamine, such as a N-substituted, for example N-lower alkylated, alkyleneamine, azaalkyleneamine, or oxealkyleneamine, for example N-methyl-piperidine or N-methyl-morpholine, or 2,3,4,6,7,8-hexahydro-pyrrolo[1,2-a]pyrimidine (diazabicyclononene; DBN), or a tertiary aromatic amine such as a di-lower alkylaniline, for example N,N-dimethylaniline, or above all a tertiary heterocyclic, monocyclic or bicyclic, base, such as quinoline or isoquinoline, especially pyridine, preferably in the presence of a solvent, such as an optionally halogenated, for example chlorinated, aliphatic or aromatic hydrocarbon, for example methylene chloride. In this reaction, approximately equimolar amounts of the imide-halide-forming agent and of the base can be used; the latter can, however, also be present in excess or in less than equivalent amounts, for example in about 0.2-fold to about 1-fold amount, or in up to about 10-fold excess, especially about 3 to 5-fold excess.

The reaction with the imide-halide-forming agent is preferably carried out with cooling, for example at temperatures of about $-50°$ C. to about $+10°$ C., but the process can also be carried out at higher temperatures, that is to say, for example, up to about 75° C., if the stability of the starting substances and the stability of the products permit a higher temperature.

The imide-halide product, which is usually further processed without isolation, is reacted, in accordance with the process, with an alcohol, preferably in the presence of one of the abovementioned bases, to give the iminoether. Suitable alcohols are, for example, aliphatic as well as araliphatic alcohols, above all optionally substituted, such as halogenated, for example chlorinated lower alkanols, or lower alkanols possessing additional hydroxyl groups, for example ethanol, n-propanol, isopropanol or n-butanol, especially methanol, as well as 2,2,2-trichloroethanol, and also optionally substituted phenyl-lower alkanols, such as benzyl alcohol. Usually an excess, for example an up to 100-fold excess, of the alcohol is employed, and the process is preferably carried out with cooling, for example at temperatures of about $-50°$ C. to about 10° C.

The iminoether product can advantageously be split without isolation. The splitting of the iminoether can be achieved by treatment with a suitable hydroxy compound. For this, water, or an aqueous mixture of an organic solvent, such as an alcohol, especially a lower alkanol, for example methanol, is preferably used. The process is usually carried out in an acid medium, for example at a pH-value of about 1 to about 5, and this value can be adjusted, if necessary, by adding a basic agent, such as an aqueous alkali metal hydroxide, for example sodium hydroxide or potassium hydroxide, or an acid, for example a mineral acid or organic acid, such as hydrochloric acid, sulphuric acid, phosphoric acid, fluoboric acid, trifluoroacetic acid or p-toluenesulphonic acid.

The three-stage process, described above, for splitting off an acyl group is advantageously carried out without isolation of the imide-halide and iminoether intermediate products, usually in the presence of an organic solvent which is inert towards the reactants, such as an optionally halogenated hydrocarbon, for example methylene chloride, and/or in an inert gas atmosphere, such as a nitrogen atmosphere.

If the imide-halide intermediate product obtainable according to the above process, instead of being reacted with an alcohol, is reacted with a salt, such as an alkali metal salt, of a carboxylic acid, especially of a sterically hindered carboxylic acid, a compound of the formula I is obtained, wherein both $R_1{}^a$ and $R_1{}^b$ represent acyl groups.

In a compound of the formula I wherein both radicals $R_1{}^a$ and $R_1{}^b$ represent acyl groups, one of these groups, preferably the group which is less sterically hindered, can be removed selectively, for example by hydrolysis or aminolysis.

In a compound of the formula I, wherein $R_1{}^A$ and $R_1{}^b$ together with the nitrogen atom represent a phthalimido group, this group can be converted into the free amino group, for example by hydrazinolysis, that is to say on treating such a compound with hydrazine.

Certain acyl radicals of an acylamino grouping in compounds obtainable according to the invention, especially the 5-amino-5-carboxyvaleryl radical, can also be split off by treatment with a nitrosylating agent, such as nitrosyl chloride, with a carbocyclic arene-diazonium salt, such as benzenediazonium chloride, or with an agent which releases positive halogen, such as a N-halogeno-amide or N-halogenoimide, for example N-bromosuccinimide, preferably in a suitable solvent or solvent mixture, such as formic acid together with a nitro-lower alkane or cyano-lower alkane, mixing the reaction product with a hydroxyl-containing agent, such as water or a lower alkanol, for example methanol, and, where necessary, working up to the free amino compound according to methods which are in themselves known.

A formyl group $R_1{}^A$ can also be removed by treatment with an acid agent, for example, p-toluenesulphonic acid or hydrochloric acid, a weakly basic agent, for example dilute ammonia, or a decarbonylating agent, for example tris(triphenylphosphine)-rhodium chloride.

A triarylmethyl group, such as a trityl group $R_1{}^A$, can, for example, be removed by treatment with an acid agent, such as a mineral acid, for example hydrochloric acid.

In a compound of the formula I, wherein $R_1{}^a$ and $R_1{}^b$ represent hydrogen, the free amino group can be acylated according to acylation methods which are in themselves known, for example by treatment with carboxylic acids or reactive acid derivatives thereof, such as halides, for example fluorides or chlorides, or anhydrides (by which there are also to be understood the internal anhydrides of carboxylic acids, that is to say ketenes, or of carbamic acids or thiocarbamic acids, that is to say isocyanates or isothiocyanates, or mixed anhydrides, such as those which can, for example, be formed with chloroformic acid lower alkyl esters, such as chloroformic acid ethyl esters, or trichloroacetic acid chloride), or activated esters, or with substituted formimino derivatives, such as substituted N,N-dimethylchloroformimino derivatives, or a N-substituted N,N-diacylamine, such as a N,N-diacylated aniline, the reaction being carried out in the presence of suitable condensation agents if necessary, for example in the presence of carbodiimides, such as dicyclohexylcarbodiimide, when using acids, or in the presence of, for example, basic agents, such as triethylamine or pyridine, when using reactive acid derivatives, it also being possible, where appropriate, to start from salts, for example ammonium salts of compounds of the formula I, wherein $R_2$ represents hydrogen.

An acyl group can also be introduced by reacting a compound of the formula I, wherein $R_1{}^a$ and $R_1{}^b$ represent hydrogen, with an aldehyde, such as an aliphatic, aromatic or araliphatic aldehyde, acylating the resulting Schiff's base, for example according to the abovementioned methods, and hydrolysing the acylated product, preferably in a neutral or weakly acid medium.

It is also possible to introduce an acyl group in stages. Thus it is, for example, possible to introduce a halogeno-lower alkanoyl group, for example bromoacetyl group, or, for example by treatment with a carbonic acid dihalide, such as phosgene, to introduce a halogenocarbonyl group, for example a chlorocarbonyl group, into a compound of the formula I having a free amino group, and to react a N-(halogeno-lower alkanoyl)-amino compound or N-(halogenocarbonyl)-amino compound, thus obtainable, with suitable exchanged reagents, such as basic compounds, for example tetrazole, thio compounds, for example 2-mercapto-1-methylimidazole, or metal salts, for example sodium azide, or alcohols, such as lower alkanols, for example tert.-butanol, and thus to obtain substituted N-lower alkanoylamino or N-hydroxycarbonylamino compounds. It is furthermore possible to react a compound of the formula I, wherein $R_1{}^a$ represents a glycyl group which is preferably substituted in the α-position, such as phenylglycyl, and $R_1{}^b$ represents hydrogen, with an aldehyde, e.g. formaldehyde, or a lower alkanone, for example, acetone, and thus to obtain compounds of the formula I, wherein $R_1{}^A$ and $R_1{}^b$ together with the nitrogen atom represent a 5-oxo-1,3-diaza-cyclopentyl residue preferably substituted in 4-position and optionally substituted in 2-position.

In both reactants, free functional groups can be transiently protected, in a manner which is in itself known, during the acylation reaction, and can be liberated after the acylation by means of methods which are in themselves known. Thus, it is possible to protect, for example, amino or carboxyl groups in the acyl residue during the acylation reaction, for example, in the form of acylamino groups, e.g. as 2,2,2-trichloroethoxycarbonylamino, 2-bromoethoxycarbonylamino or tert.-butyloxycarbonylamino groups, and in the form of esterified carboxyl groups, e.g. as a diphenylmethoxycarbonyl group, and then, optionally after having converted the protective group, for example, a 2-bromoethoxycarbonyl into the 2-iodoethoxycarbonyl group, to split such protected groups, for example, by treatment with reducing agents, e.g. zinc in the presence of aqueous acetic acid, or trifluoroacetic acid, or by hydrogenolysis.

The acylation can also be effected by replacing an already existing acyl group by a different, preferably sterically hindered, acyl group, for example according to the process described above, by preparing the imide-halide compound, treating this with a salt of an acid, and hydrolytically splitting off one of the acyl groups present in the product thus obtainable, usually the less sterically hindered acyl group.

In a compound of the formula I, wherein $R_1{}^a$ and $R_1{}^b$ represent hydrogen, the free amino group can also be protected by introducing a triaryl methyl group, for example by treatment with a reactive ester of a triarylmethanol, such as trityl chloride, preferably in the presence of a basic agent, such as pyridine.

An amino group can also be protected by introducing a silyl and stannyl group. Such groups are introduced in a manner which is in itself known, for example by treatment with a suitable silylating agent, such as a tri-lower alkylsilyl halide, for example trimethyl-silyl chloride, or an optionally N-mono-lower alkylated, N,N-di-lower alkylated, N-tri-lower alkylsilylated or N-lower alkyl-N-tri-lower alkylsilylated N-(tri-lower alkyl-silyl)-amine (see, for example, British Pat. No. 1,073,530) or with a suitable stannylating agent, such as a bis-(tri-lower alkyl-tin)oxide, for example bis-(tri-n-butyl-tin)-oxide, a tri-lower alkyl-tin hydroxide, for example triethyl-tin hydroxide, a tri-lower alkyl-lower alkoxy-tin compound, tetra-lower alkoxy-tin compound or tetra-lower alkyl-tin compound, or a tri-lower alkyl-tin halide, for example tri-n-butyl-tin chloride (see, for example, Netherlands Published Specification 67/17107).

In a compound of the formula I, obtainable according to the process, which possesses a group of the formula —C(=O)—O—$R_2$, wherein $R_2$ represents hydrogen, the free carboxyl group can be esterified, in a manner which is in itself known, to give a protective carboxyl group, for example, by treatment with a diazo compound, such as a diazo-lower alkane, for example diazomethane or diazoethane, or a phenyldiazo-lower alkane, for example phenylidiazomethane or diphenyldiazomethane, or by reaction with an alcohol which is suitable for esterification, in the presence of an esterifying agent, such as a carbodiimide, for example dicyclohexylcarbodiimide, as well as carbonyldiimidazole, or according to any other known and suitable esterification process, such as reaction of a salt of the acid with a reactive ester of an alcohol and a strong inorganic acid, as well as a strong organic sulphonic acid. Furthermore, it is possible to convert acid halides, such as acid chlorides (manufactured, for example, by treatment with oxalyl chloride), activated esters (formed, for example, with N-hydroxy-nitrogen compounds) or mixed anhydrides (formed, for example, with halogenoformic acid lower alkyl esters, such as chloroformic acid ethyl ester, or with halogenoacetic acid halides, such as trichloroacetic acid chloride), into an esterified carboxyl group by reaction with alcohols, optionally in the presence of a base, such as pyridine.

Mixed anhydrides can be manufactured by reacting a compound of the formula I, wherein $R_2$ represents hydrogen, and preferably a salt thereof, especially an alkali metal salt or ammonium salt thereof, with a reactive derivative, such as a halide, for example the chloride, or an acid, for example a halogenoformic acid lower alkyl ester or a lower alkanecarboxylic acid chloride.

In a resulting compound, a grouping of the formula —C(=O)—O—$R_2{}^A$ can be converted into another group of this formula, for example 2-chloroethoxycarbonyl or 2-bromoethoxycarbonyl of the formula —C(=O)—O—$R_2{}^a$ can be converted into 2-iodoethoxycarbonyl by treatment with an iodine salt, such as sodium iodide, in the presence of a suitable solvent, such as acetone.

Carboxyl groups protected by organic silyl groups or stannyl groups can be formed in a manner which is in itself known, for example by treating compounds of the formula I, wherein $R_2$ represents hydrogen, or salts, such as alkali metal salts, for example sodium salts, thereof, with a suitable silylating agent or stannylating agent, such as one of the abovementioned silylating agents or stannylating agents; see, for example, British Pat. No. 1,073,530 or Netherlands Published Specification No. 67/17107.

In a compound of the formula I, obtainable according to the invention, which has an esterified carboxyl group, with the latter representing, for example, an esterified carboxyl group of the formula $-C(=O)-O-R_2^A$ which can easily be converted into the free carboxyl group, the former group can be converted into the free carboxyl group in a manner which is in itself known, for example depending on the nature of the esterifying radical $R_2^A$; a grouping of the formula $-C(=O)-OR_2^a$ or $-C(=O)-OR_2^b$ can, for example, be converted by treatment with a chemical reducing agent, such as a metal, for example zinc, or a reducing metal salt, such as a chromium-II salt, for example chromium-II chloride, usually in the presence of a hydrogen-donating agent, which together with the metal can generate nascent hydrogen, such as an acid, above all acetic acid, or formic acid, or in the presence of an alcohol, to which water is preferably added; a grouping of the formula $-C(=O)-OR_2^c$ can, for example, be converted by irradiation, preferably with ultraviolet light, using shorter-wave-ultraviolet light, for example below 290 m$\mu$, if $R_2^c$ for example represents a benzyl radical which is optionally substituted in the 3-, 4- and/or 5-position, for example by lower alkoxy groups and/or nitro groups, or using longer wave ultraviolet light, for example above 290 m$\mu$, if $R_2^c$ denotes, for example, a benzyl radical substituted in the 2-position by a nitro group; a grouping $-C(=O)-OR_2^d$ can, for example, be converted by treatment with a suitable acid agent, such as formic acid or trifluoroacetic acid, optionally with the addition of a nucleophilic compound, such as phenol or anisole; a grouping $-C(=O)-OR_2^e$ can be converted by hydrolysis, for example by treatment with a weakly acid, or especially with a weakly basic, aqueous agent, such as aqueous sodium dicarbonate or an aqueous potassium phosphate buffer of pH about 7 to about 9; and a grouping $-C(=O)-OR_2^f$ can be converted by hydrogenolysis, for example by treatment with hydrogen in the presence of a noble metal catalyst, for example a palladium catalyst.

A carboxyl group which is protected, for example by silylation or stannylation, can be liberated in the usual manner, for example by treatment with water or with an alcohol.

Resulting compounds can be converted into one another in a manner which is in itself known. Thus it is possible, for example, to liberate modified functional groups, such as acylated amino groups or esterified carboxyl groups, in accordance with methods which are in themselves known, for example those described above, or functionally to modify, for example acylate or esterify, or substituted, free functional groups, such as amino or carboxyl groups, according to processes which are in themselves known. Thus, for example, an amino group can be converted into a sulphoamino group by treatment with sulphur trioxide, preferably in the form of a complex with an organic base, such as a tri-lower alkylamine, for example triethylamine. It is furthermore possible to react the reaction mixture of an acid addition salt of a 4-guanylsemicarbazide with sodium nitrite with a compound of the formula I, wherein, for example, the amino protective group $R_1^A$ represents an optionally substituted glycyl group, and thus to convert the amino group into a 3-guanylureido group.

Salts of compounds of the formula I can be manufactured in a manner which is in itself known. Thus it is possible to form salts of compounds of the formula I, wherein $R_2$ represents hydrogen, for example by treatment with metal compounds, such as alkali metal salts of suitable carboxylic acids, for example the sodium salt of $\alpha$-ethyl-caproic acid, or with ammonia or a suitable organic amine, for which purpose stoichiometric amounts, or only a slight excess of the salt-forming agent, are preferably used. Acid addition salts of compounds of the formula I having basic groupings are obtained in the usual manner, for example by treatment with an acid or with a suitable anion exchange reagent. Internal salts of compounds of the formula I, which contain a salt-forming amino group and a free carboxyl group, can, for example, be formed by neutralisation of salts, such as acid addition salts, to the isoelectric point, for example with weak bases, or by treatment with liquid ion exchangers.

Salts can be converted into the free compounds in the usual manner; metal salts and ammonium salts can, for example, be converted by treatment with suitable acids, and acid addition salts can, for example, be converted by treatment with a suitable basic agent.

Resulting mixtures of isomers can be separated into the individual isomers according to methods which are in themselves known, for example by fractional crystallisation, adsorption chromatography (column chromatography or thin layer chromatography) or other suitable separation processes. Resulting racemates can be separated into the antipodes in the usual manner, where appropriate after introduction of suitable salt-forming groupings, for example by forming a mixture of diastereoisomeric salts with optically active salt-forming agents, separating the mixture into diastereoisomeric salts, and converting the separated salts into the free compounds, or by fractional crystallisation from optically active solvents. fractional crystallisation from optically active solvents.

The process also encompasses those embodiments according to which compounds arising as intermediate products are used as starting substances and the remaining process stages are carried out with these, or the process is stopped at any state; furthermore, starting substances can be used in the form of derivatives or formed during the reaction.

Preferably, such starting substances are used, and the reaction conditions are so chosen, that the compounds initially mentioned as being particularly preferred are obtained.

The starting substances of the formula II used according to the process can, for example, be manufactured by converting the hydroxyl group in a compound of the formula

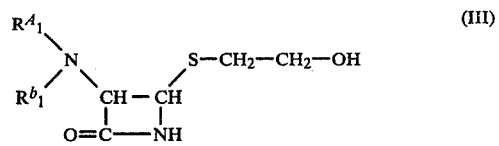

into a hydroxyl group esterified by the acyl radical of the formula $-C(=O)-X$, wherein X represents an etherified hydroxyl group, which together with the carbonyl grouping forms an esterified carboxyl group which can be split under mild conditions.

The compound of the formula

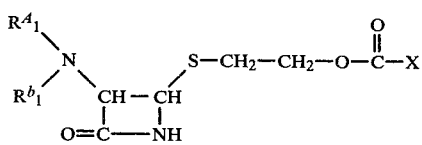

thus obtainable is reacted with a compound of the formula

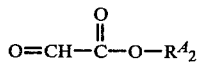

or a reactive derivative thereof, and in the addition compound of the formula

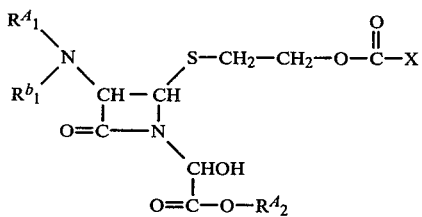

the secondary hydroxyl group is converted into a reactive esterified hydroxyl group. The reactive ester of the formula

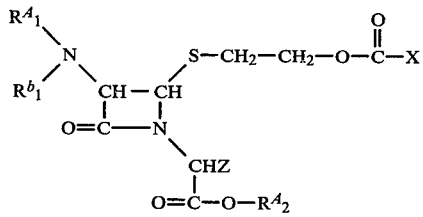

wherein Z represents a reactive esterified hydroxyl group, above all a halogen atom, especially a chlorine or bromine atom, or an organic sulphonyloxy group, for example a 4-methylphenylsulphonyloxy or methylsulphonyloxy group, is reacted with a phosphine compound of the formula

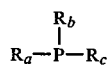

wherein each of the radicals $R_a$, $R_b$ and $R_c$ has the above-mentioned meanings and represents an optionally substituted hydrocarbon radical, and this yields, if necessary after splitting off the elements of an acid of the formula H-Z (IXb) from a phosphonium salt compound of the formula

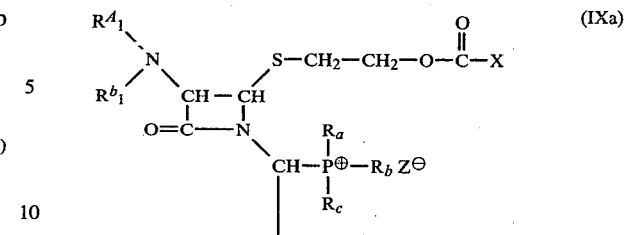

obtainable as an intermediate product, the phosphoranylidene compound of the formula

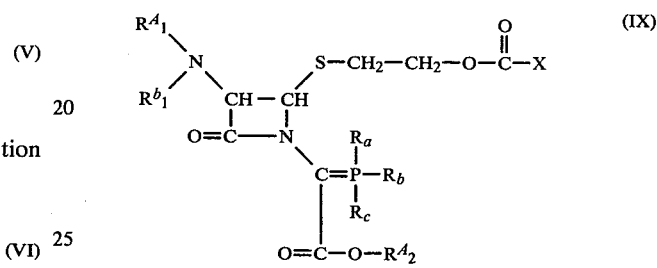

in which the esterified carboxyl grouping —C(=O)—X is split, thus producing the starting material of the formula II.

In a compound of the formula III, the hydroxyl group is converted, in a manner which is in itself known, by acylation, into the acyloxy group of the formula —O—C(=O)—X, especially into one of the groups of the formulae —O—C(=O)—O—$R_0{}^a$, —O—C(=O)—O—$R_0{}^b$, —O—C(=O)—O—$R_0{}^c$, —O—C(=O)—O—$R_0{}^d$ and —O—C(=O)—O—$R_0{}^e$, wherein $R_0{}^a$, $R_0{}^b$, $R_0{}^c$, $R_0{}^d$ and $R_0{}^e$ have the meanings corresponding to the radicals $R_2{}^a$, $R_2{}^b$, $R_2{}^c$, $R_2{}^d$ or $R_2{}^e$, and above all represent 2,2,2-trichloroethyl, phenacyl, 4,5-dimethoxy-2-nitrobenzyl or tert.-butyl radicals. In this reaction, the usual acylating agents can be used, such as acids, and especially suitable reactive derivatives of acids, if necessary in the presence of a condensation agent, an acid for example being used in the presence of a carbodiimide and an acid derivative in the presence of a basic agent, such as an organic tertiary base, for example triethylamine or pyridine. Reactive derivatives of acids are, for example, anhydrides including internal anhydrides such as ketenes, or isocyanates, or mixed anhydrides, which can in particular be prepared with halogenoformic acid esters, for example chloroformic acid ethyl ester, or halogenoacetic acid halides, for example trichloroacetic acid chloride, and also halides, above all chlorides, or reactive esters, such as esters of acids with alcohols or phenols containing electron-attracting groupings, or esters with N-hydroxy compounds, for example cyanomethanol, 4-nitrophenol or N-hydroxysuccinimide. At the same time, the acyl group can also be introduced in stages; thus, for example, a compound of the formula III can be treated with a carbonic acid dihalide, for example phosgene; and the compound of the formula IV thus obtainable, wherein X represents a halogen atom, for example a chlorine atom, can be converted into the desired compound of the formula IV by reaction with a suitable alcohol, for example 2,2,2-trichloroethanol, tert.-butanol or phenacyl alcohol. The acylation reaction can be carried out in the presence or absence of solvent or solvent mixtures, if necessary whilst cooling or warming, in a closed vessel under pressure and/or in an inert gas atmosphere, for example a nitrogen atmosphere, in stages if desired.

The addition of the glyoxylic acid ester compound of the formula V to the nitrogen atom of the lactam ring of a compound of the formula IV preferably takes place at elevated temperature, above all at about 50° C. to about 150° C., and in particular in the absence of a condensation agent and/or without the formation of a salt. Instead of the free glyoxylic acid ester compound, a reactive oxo derivative thereof, above all a hydrate, can also be used, and the water produced when using the hydrate can, if necessary, be removed by distillation, for example azeotropically.

The process is preferably carried out in the presence of a suitable solvent, such as, for example dioxane or toluene, or solvent mixture, if desired or required in a closed vessel under pressure and/or in the atmosphere of an inert gas, such as nitrogen.

In a compound of the formula VI, the secondary hydroxyl group can be converted, in a manner which is in itself known, into a reactive hydroxyl group esterified by a strong acid, especially into a halogen atom or into an organic sulphonyloxy group. For this, for example, suitable halogenating agents, such as a thionyl halide, for example thionyl chloride, a phosphorus oxyhalide, especially phosphorus oxychloride, or a halogenophosphonium halide, such as triphenylphosphonium dibromide or triphenylphosphonium diiodide, or a suitable organic sulphonic acid halide, such as a sulphonic acid chloride, are used, and the reaction is preferably carried out in the presence of a basic agent, above all an organic basic agent, such as an aliphatic tertiary amine, for example triethylamine or diisopropylethylamine, or a heterocyclic base of the pyridine type, for example pyridine or collidine. Preferably, the process is carried out in the presence of a suitable solvent, for example dioxane or tetrahydrofurane, or of a solvent mixture, if necessary with cooling and/or in the atmosphere of an inert gas, such as nitrogen.

In a resulting compound of the formula VII, a reactive esterified hydroxyl group Z can be converted, in a manner which is in itself known, into another reactive esterified hydroxyl group. Thus it is for example possible to replace a chlorine atom by a bromine or iodine atom by treating the corresponding chlorine compound with a suitable bromine or iodine reagent, especially with an inorganic bromide or iodide salt, such as lithium bromide, preferably in the presence of a suitable solvent, such as ether, or to replace a suitable organic sulphonyloxy group, such as the methylsulphonyloxy group, by a halogen atom, for example a chlorine atom, in the presence of halogen ions such as chloride ions.

The reaction of a compound of the formula VII with the phosphine compound of the formula VIII, wherein each of the groups $R_a$, $R_b$ and $R_c$ above all represent phenyl, or a lower alkyl radical, especially the n-butyl radical, is preferably carried out in the presence of a suitable inert solvent, such as an aliphatic, cycloaliphatic or aromatic hydrocarbon, for example hexane, cyclohexane, benzene or toluene, or of an ether, for example dioxane, tetrahydrofurane or diethylene glycol-dimethyl ether, or of a solvent mixture. If necessary, the process is carried out with cooling or at elevated temperature and/or in the atmosphere of an inert gas, such as nitrogen.

A phosphonium salt compound of the formula IXa formed as an intermediate usually spontaneously loses the elements of the acid of the formula H-Z (IXb); if necessary, the phosphonium salt compound can be decomposed by treatment with a weak base, such as an organic base, for example diisopropylethylamine or pyridine, and be converted into the phosphoranylidene compound of the formula IX.

The splitting of the esterified carboxyl group of the formula $—C(=O)—X$ into a compound of the formula IX can be carried out in various ways, depending on the nature of the group X.

Thus a grouping $—C(=O)—X$, wherein X represents the group of the formula $—O—R_0^a$ and $—O—R_0^b$, can be split by treatment with a chemical reducing agent under mild conditions, in most cases at room temperature or even with cooling.

Chemical reducing agents are, for example, reducing metals, as well as reducing metal compounds, for example metal alloys or metal amalgams, and also strongly reducing metal salts. The following are particularly suitable: zinc, zinc alloys, for example zinc-copper, or zinc amalgam, and also magnesium, which are preferably used in the presence of hydrogen-donating agents which can, together with the metals, metal alloys and metal amalgams, generate nascent hydrogen, zinc for example being used advantageously in the presence of acids, such as organic carboxylic acids, for example lower alkanecarboxylic acids, above all acetic acid, or acid agents, such as ammonium chloride or pyridine hydrochloride, preferably with the addition of water, or in the presence of alcohols, especially aqueous alcohols, such as lower alkanols, for example methanol, ethanol or isopropanol, which can, if desired, be used conjointly with an organic carboxylic acid, and alkali metal amalgams, such as sodium amalgam or potassium amalgam, or aluminium amalgam, in the presence of moist solvents, such as ethers or lower alkanols.

Strongly reducing metal salts are, above all, chromium-II salts, for example chromium-II chloride or chromium-II acetate, which are preferably used in the presence of aqueous media, containing organic solvents which are miscible with water, such as lower alkanols, carboxylic acids, such as lower alkanecarboxylic acid, or derivatives, such as optionally substituted, for example lower alkylated, amides thereof, or ethers, for example methanol, ethanol, acetic acid, dimethylformamide, tetrahydrofurane, dioxane, ethylene glycoldimethyl ether or diethylene glycol-dimethyl ether.

In a compound of the formula IX, wherein X represents a radical of the formula $—O—R_0^c$, the group of the formula $—C(=O)—X$ can be split by irradiation with light, preferably with ultraviolet light. For this, light of longer or shorter wavelength is used, depending on the nature of the substituent $R_0^c$. Thus, for example, groups of the formula $—C(=O)—O—R_0^c$, wherein $R_0^c$ represents an arylmethyl radical, especially benzyl radical, which is substituted by a nitro group in the 2-position of the aryl radical and optionally possesses further substituents, such as lower alkoxy groups, for example methoxy groups, for example the 4,5-dimethoxy-2-nitro-benzyl radical, are split by irradiation with ultraviolet light with a wavelength range of over 290 mu, for example at a main wavelength range of about 315 mu (high pressure mercury vapor lamp, preferably with a Pyrex glass filter), and those in which $R_0^c$ for example represents an arylmethyl radical, for example benzyl radical, which is optionally substituted in the 3-, 4- and/or 5-position, for example by lower alkoxy and/or nitro groups. are split by irradiation with ultraviolet light with a wavelength range of below 290 mµ. In the former case, a high pressure mercury vapour lamp is used, preferably employing Pyrex glass as the filter, for example at a main wavelength range of about 315 mµ, and in the latter case a low pressure mercury vapour lamp is used, for example at main wavelength range of about 254 mµ.

The irradiation reaction is carried out in the presence of a suitable polar or non-polar organic solvent or of a mixture; solvents are, for example, optionally halogenated hydrocarbons, such as optionally chlorinated lower alkanes, for example methylene chloride, or optionally chlorinated benzenes, for example benzene, and also alcohols, such as lower alkanols, for example methanol or ketones, such as lower alkanones, for example acetone. The reaction is preferably carried out at room temperature or, if desired, with cooling, usually in an inert gas atmosphere, or example a nitrogen atmosphere.

An esterified carboxyl grouping —C(=O)—O—$R_0^d$ can be split by treatment with an acid agent, especially with an acid such as a strong organic carboxylic acid, for example an optionally substituted lower alkane carboxylic acid which preferably contains halogen atoms, such as trifluoroacetic acid, and also with formic acid or a strong organic sulphonic acid, for example p-toluenesulphonic acid. For this, an excess of an acid reagent which is liquid under the reaction conditions is usually employed as the diluent, and the process is carried out at room temperature or with cooling, for example to between about −20° C. and about +10° C.

An esterified carboxyl grouping —C(=O)—O—$R_0^c$ can be split hydrolytically, depending on the radical $R_0^e$ also under weakly acid or weakly basic conditions, for example at a pH value of about 7 to about 9, such as by treatment with an acid, with a suitable aqueous buffer solution, for example phosphate buffer solution, or with an alkali metal bicarbonate, such as sodium bicarbonate or potassium bicarbonate, in the presence of water and preferably of an organic solvent, such as methanol or acetone.

In a compound of the formula IX, the esterified carboxyl groups of the formulae —C(=O)—X and —C(=O)—O—$R_2^A$ usually differ from one another in such a way that under the conditions of the splitting the esterified carboxyl group of the formula —C(=O)—X, the esterified carboxyl group of the formula —C(=O)—O—$R_2^A$ remains intact. If, for example, the esterified carboxyl group of the formula —C(=O)—X represents an esterified carboxyl group which can be split on treatment with a chemical reducing agent, such as zinc in the presence of aqueous acetic acid, for example represents a grouping of the formula —C(=O)—O—$R_0^a$ or —C(=O)—O—$R_0^b$, wherein $R_0^a$ preferably represents the 2,2,2-trichloroethyl radical, and $R_0^b$ above all represents the phenacyl group, then the esterified carboxyl group of the formula —C(=O)—O—$R_2^A$ for example represents an esterified carboxyl group —C(=O)—O—$R_2^A$ which can be split on treatment with a suitable acid, such as trifluoroacetic acid, for example a grouping of the formula —C(=O)—O—$R_2^d$, wherein $R_2^d$ preferably represents the tert.-butyl group.

The intermediate products of the formula III are for example obtained if a penam-3-carboxylic acid compound Xa of formula

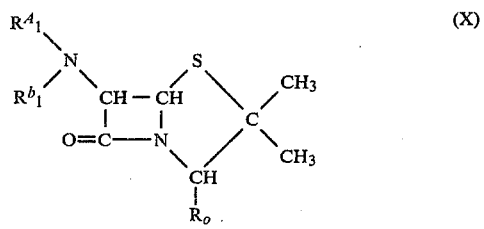

wherein $R_1^A$ above all represents an acyl group Ac and $R_1^b$ represents hydrogen, with free functional groups, such as hydroxyl, mercapto and especially amino and carboxyl groups in an acyl radical Ac optionally being protected, for example by acyl groups or in the form of ester groups, and $R_0$ represents a carboxyl group —C(=O)—OH (compound Xa), or a salt thereof, is converted into the corresponding acid azide compound of the formula X, wherein $R_0$ represents the azidocarbonyl radical —C(=O)—$N_3$ (compound Xb), this compound is converted, with elimination of nitrogen, to the corresponding isocyanate compound of the formula X, wherein $R_0$ denotes the isocyanate group —N=C=O (compound Xc), and this compound is simultaneously or subsequently treated with a compound of the formua H-$X_0$ (XI), wherein $X_0$ represents an etherified hydroxyl group, which together with a carbonyl grouping represents an esterified carboxyl group of the formula —C(=O)—$X_0$ which can split under neutral or weakly acid conditions.

A penam compound of the formula

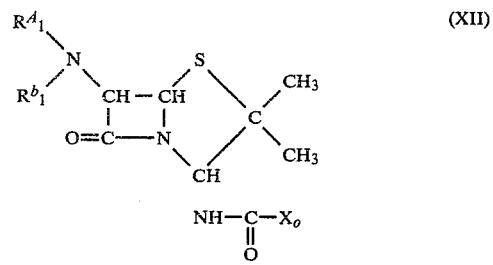

is thus obtained in which an amino protective group $R_1^A$ and/or $R_1^b$ is replaced by hydrogen, for example according to the process described above, and, if desired, an amino protective group which can be split off under the following reaction conditions is introduced into the free amino group, for example by acylation. In a penam compound of the formula

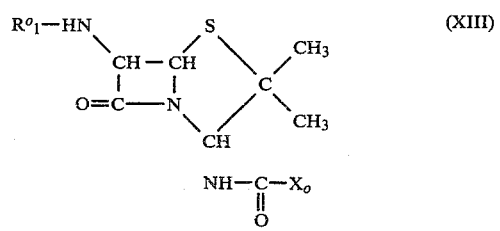

thus obtainable, wherein $R_1^0$ represents hydrogen or an acyl group $Ac_0$ which can be split off under the conditions of the following reaction, the substituted hydroxycarbonyl group of the formula —C(=O)—$X_0$, which is splittable under neutral or weakly acid conditions, can be split with simultaneous or subsequent treatment with water, and the 4,4-dimethyl-5-thia-2,7-diazabicyclo[4.2.0]oct-2-en-8-one which may be obtained can be isolated, or the carbon-nitrogen double bond therein can be reduced. 3-isopropyl-4-thia-2,6-diazabicyclo[3.2.0]heptan-7-one of the formula

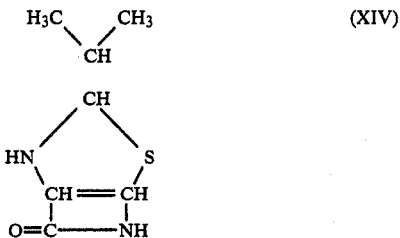

is thus obtained. Oxidation of the compound of the formula XIV or of the 3,3-dimethyl-4-thia-2,6-diazabicyclo[3.2.0]heptan-7-one of the formula

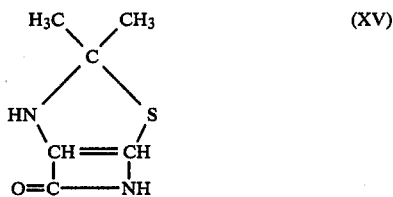

which can, for example, be manufactured according to the process described in Austrian Patent No. 263,768 or in German Published Specification No. 1.935.637, yields, if required after treatment with water, the bis-(cis-3β-amino-2-oxo-4β-azetidinyl)-disulphide of the formula

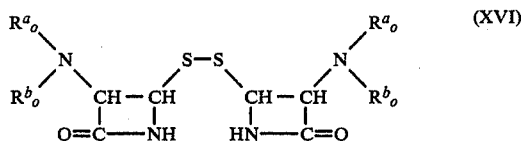

in which $R_0{}^a$ and $R_0{}^b$ represent hydrogen or together represent the isopropylidene or 1-isobutylidene group, or a salt thereof, especially an acid addition salt thereof. In such a compound, amino protective groups, $R_1{}^A$ and/or $R_1{}^b$ are introduced into the amino groups, acyl groups for example being introduced by acylation, and an isopropylidene or 1-isobutylidene group which may be formed by $R_0{}^a$ and $R_0{}^b$ is split off under the reaction conditions, if appropriate in a modified form. The compound of the formula XVIa thus obtainable, wherein $R_0{}^a$ denotes an amino protective group $R_1{}^A$, and $R_0{}^b$ denotes or an acyl group Ac, is reacted with ethylene oxide with simultaneous treatment with a reducing agent, and the intermediate product of the formula III is thus obtained.

Acyl groups Ac occurring in compounds of the formula X can represent any acyl radicals of organic carboxylic acids with optionally protected functional groups, above all acyl radicals contained in fermentatively or biosynthetically available N-acyl derivatives of 6-amino-penam-3-carboxylic acid compounds, such as a monocyclic arylacetyl or aryloxyacetyl radical, and also an optionally substituted lower alkanoyl or lower alkenoyl radical, for example the 4-hydroxy-phenylacetyl, hexanoyl, octanoyl, 3-hexenoyl, 5-amino-5-carboxy-valeroyl, n-butyl-thioacetyl or allylthioacetyl radical, especially the phenylacetyl or phenyloxyacetyl radical, or an acyl radical which can easily be split off, preferably under acid conditions, such as one of the above mentioned acyl radicals of half-esters of carbonic acid.

The conversion of an acid compound Xa or of a suitable salt, especially of an ammonium salt, into the corresponding acid azide Xb can, for example, be effected by conversion into a mixed anhydride (for example, by treatment with a halogenoformic acid lower alkyl ester, such as chloroformic acid ethyl ester, in the presence of a basic agent, such as triethylamine) and treatment of such an anhydride with an alkali metal azide, such as sodium azide. The acid azide compound Xb thus obtainable can be converted into the desired isocyanate compound Xc under the reaction conditions, for example on warming, in the absence or presence of a compound of the formula XI, and the compound Xc usually does not have to be isolated and can be converted directly, in the presence of a compound of the formula XI, into the desired compound of the formula XII.

Etherified hydroxyl groups Xo form together with a carbonyl grouping an esterified carboxyl group which can be split under neutral or weakly acid conditions. These are especially the groups of the formula $—O—R_o{}^a$, $—O—R_o{}^b$ and $—O—R_o{}^c$, wherein $R_o{}^a$, $R_o{}^b$ and $R_o{}^c$ correspond to the above mentioned radicals $R_2{}^a$, $R_2{}^b$ and $R_2{}^c$.

The reaction of a compound of the formula Xc with a compound of the formula XI, especially with a 2 halogenoethanol $R_o{}^a$-OH, for example with 2,2,2-trichloroethanol or 2-bromoethanol, an arylcarbonylmethanol $R_o{}^b$-OH, for example phenacylalcohol, or an arylmethanol $R_o{}^c$-OH, for example 4,5-dimethoxy-2-nitro-benzyl alcohol, is optionally carried out in an inert solvent, for example in a halogenated hydrocarbon, such as carbon tetrachloride, chloroform or methylene chloride, or in an aromatic solvent, such as benzene, toluene or chlorobenzene, preferably with warming.

An acylamino group in an intermediate product of the formula XII, in which Ac represents an acyl group contained in fermentatively or biosynthetically available N-acyl derivatives of 6-amino-penam-3-carboxylic acid compounds can be split in a manner which is in itself known, for example, according to the process described above, if desired, after protection of functional groups in an acyl radical (for example by acylation, esterification or silylation), for example by treatment with a suitable inorganic acid halide, such as phosphorus pentachloride, preferably in the presence of a basic agent, such as pyridine, reaction of the imide-chloride with an alcohol, such as a lower alkanol, for example methanol, and splitting of the imino-ether in an aqueous medium, preferably under acid conditions. The acyl radical of a suitable half-ester of carbonic acid, such as a lower alkoxycarbonyl radical which can be removed under acid conditions, for example the tert.-butyloxycarbonyl, tert.pentyloxycarbonyl, adamantylcarbonyl or diphenylmethoxycarbonyl radical, can be removed by, for example, treatment with trifluoroacetic acid.

In an intermediate product of the formula XII, wherein $R_1{}^0$ represents hydrogen, the latter can be replaced by a suitable acyl group which can easily be removed under the subsequent reaction conditions;

such an acyl group is, for example, the acyl group of the formula $-C(=O)-X_0$, especially of the formula $-C(=O)-O-R_0{}^a$, $-C(=O)-O-R_0{}^b$ or $-C(=O)-O-R_0{}^c$. The acylation can be carried out in stages if desired, for example in accordance with the process described above.

The splitting of the substituted hydroxycarbonyl grouping of the formula $-C(=O)-X_0$ in a compound of the formula XIII can be effected in accordance with the process described above, which is appropriately modified depending on the nature of the radical $X_0$, that is to say a group of the formula $-C(=O)-O-R_0{}^a$ or $-C(=O)-O-R_0{}^b$, wherein $R_0{}^a$ above all represents the 2,2,2-trichloroethyl, furthermore the 2-iodoethyl group or the 2-bromoethyl group capable of being converted into the latter, $R_0{}^b$ in particular represents the phenacyl group, can be split, optionally after conversion of such group, for example of the 2-bromoethyl into the 2-iodoethyl group, by treatment with chemical reducing agents under neutral or weakly acid conditions, for example zinc in the presence of 90% strength aqueous acetic acid, and a group of the formula $-C(=O)-O-R_0{}^c$, wherein $R_0{}^c$ above all represents the 4,5-dimethoxy-2-nitro-benzyl group, can be split by irradiation with light, preferably with ultraviolet light, water being present during the process or during working up.

The 4,4-dimethyl-5-thia-2,7-diazabicyclo[4.2.0]oct-2-en-8-one which may be formed as an intermediate product and which arises in particular during the non-reductive splitting of a group of the formula $-C(=O)-X_0$ in the intermediate product of the formula XIII, wherein $X_0$ represents the group of the formula $-O-R_0{}^c$, and also arises during splitting of group of the formula $-C(=O)-X_0$, wherein $X_0$ represents the group of the formula $-O-R_0{}^a$, by means of a strongly reducing metal salt, can be converted by exhaustive reduction into the desired 3-isopropyl-4-thia-2,6-diazabicyclo[3.2.0]heptan-7-one or can be isolated from a mixture with the latter. For the reduction of the carbon-nitrogen double bond in the 4,4-dimethyl-5-thia-2,7-diazabicyclo[4.2.0]oct-2-en-8-one, which takes place with simultaneous rearrangement to give 3-isopropyl-4-thia-2,6-diazabicyclo[3.2.0]heptan-7-one, chemical reducing agents are preferably used, above all reducing metals or metal compounds, such as those mentioned above, preferably in the presence of hydrogen-releasing agents, especially zinc in the presence of an acid, such as acetic acid, or of an alcohol. A mixture of 3-isopropyl-4-thia-2,6-diazabicyclo[3.2.0]heptan-7-one and 4,4-dimethyl-5-thia-2,7-diazabicyclo[4,2,0]-2-en-8-one, such as can be produced above all on reductive splitting of the group of the formula $-C(=O)-X_0$ in an intermediate product of the formula XIII, wherein $X_0$ denotes a group of the formula $-O-R_0{}^a$, is separated into the individual compounds according to methods of separation which are in themselves known, for example by fractional crystallisation, adsorption chromatography (column chromatography or thin layer chromatography) or other suitable separation processes.

The oxidation of compounds of the formulae XIV and XV can be carried out with the aid of oxidising agents usually employed for the manufacture of disulphide compounds, such as oxygen or hydrogen peroxide (preferably in the presence of heavy metal salts, such as copper-II salts or iron-III salts, for example the halides or sulphates, as catalysts), halogen, especially iodine, hypohalites, alkali metal hypohalites, iron-III chloride, or heavy metal acylates, such as lead acylates, for example lead tetraacetate, usually in the presence of a suitable diluent, such as benzene, ethanol, acetone or acetic acid, optionally in the presence of water.

Usually, amino protective groups are introduced into the amino groups of the crude disulphide in accordance with the process described above, an acyl group for example being introduced by treatment with an acid or a derivative thereof, for example a halide, if necessary stepwise and/or in the presence of a suitable condensation agent or basic agent, and a triarylmethyl group, for example the trityl group, by treatment with a reactive ester of a triarylmethanol, such as a trityl halide, for example trityl chloride, preferably in the presence of a basic agent, such as pyridine. Isopropylidene or 1-isobutylidene groups which may be present can be split off previously or simultaneously.

Possible reducing agents which can simultaneously be used when treating a compound of the formula XVI, wherein $R_0{}^a$ denotes an amino protective group and $R_0{}^b$ denotes hydrogen or an acyl group, with ethylene oxide, are, for example, the abovementioned chemical reducing agents, the reaction being carried out in a neutral or weakly acid medium. Zinc, which is employed in the presence of aqueous acetic acid, is particularly suitable as a reducing agent.

At any suitable stage in the manufacture of the starting substances, additional measures can be performed on intermediate products, by means of which they can be converted into other intermediate products of the same type; additional measures of this nature are, for example, carried out according to the processes described above which are employed in the conversion of the final substances. In a starting material of the formula II, for example, the bromine atom in a 2-bromoethyl radical $R_2{}^A$ can be replaced by an iodine atom, for example by treatment with an alkali metal iodide, such as sodium iodide, in the presence of a suitable solvent, such as acetone.

In the manufacture of the starting substances it is possible, if necessary, temporarily to protect, in a manner which is in itself known, free functional groups in the reactants which do not participate in the reaction, for example free hydroxyl, mercapto and amino groups, for example by acylation, tritylation or silylation, and free carboxyl groups, for example by esterification, including silylation, and to liberate these groups, if desired, in a manner which is in itself known, after the reaction has taken place.

The pharmacologically useful compounds of the present invention can, for example, be used for the manufacture of pharmaceutical preparations which contain an effective amount of the active substance together or in conjunction with inorganic or organic, solid or liquid, pharmaceutically useful excipients, which are suitable for enteral, parenteral or topical administration. Preferably, tablets or gelatine capsules are used which contain the active substance together with diluents, for example, lactose, dextrose, sucrose, mannitol, sorbitol, cellulose and/or glycine, and lubricants, for example, silica, talc, stearic acid or salts thereof, such as magnesium or calcium stearate, and/or polyethylene glycol; tablets may also contain binders, for example, magnesium aluminium silicate, starches, such as corn starch, wheat starch, rice starch or arrowroot starch, gelatine, tragacanth, methylcellulose, sodium carboxymethylcellulose and/or polyvinylpyrrolidone and, if desired, disintegrating agents, for example, starches, agar, alginic acid or sodium alginate, or effervescing mixtures and/or adsorbents, dyestuffs, flavors and sweeteners. Injectable preparations are preferably isotonic aqueous solutions or suspensions, suppositories and ointments primarily fat emulsions or suspensions. The pharmaceutical preparations can be sterilised and/or may contain auxiliary substances, for example, preservatives, stabilisers, wetting agents and/or emulsifiers, solubilisers, salts for regulating the osmotic pressure and/or buffers. The present pharmaceutical preparations are manufactured in a manner which is in itself known, for example, by means of conventional mixing, granulating or dragee-making processes, and contain from about 0.1% to about 75%, especially from about 1% to about 50%, of the active substance and can, if desired, contain further pharmacologically valuable substances.

The examples which follow serve to illustrate the invention. The temperatures are given in degrees Centigrade.

EXAMPLE 1

A mixture of 0.221 g of crude α-[4,3-(2-hydroxyethyl-mercapto)-2-oxo-3β-(N-phenylacetylamino)-1-azetidinyl]-α-triphenylphosphoranylidene-acetic acid tert.-butyl ester in 5 ml of dimethylsulphoxide and 5 ml of acetic anhydride is left to stand for 16 hours at room temperature and is then concentrated under reduced pressure. The residue is taken up in 100 ml of toluene; the organic solution is washed three times with 50 ml of distilled water at a time, dried over sodium sulphate and evaporated. The oily residue is chromatographed on 10 g of silica gel; the desired 7β-(N-phenylacetylamino)-ceph-3-em-4-carboxylic acid tert.-butyl ester of the formula

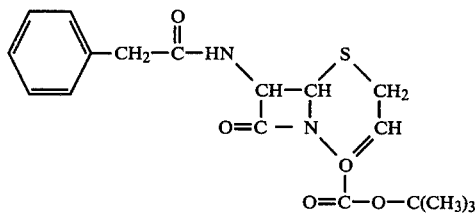

which forms by cyclisation of the β-[4β-formylmethyl-mercapto-2-oxo-3β-(N-phenylacetyl-amino)-1-azetidinyl]-α-triphenylphosphoranylidene-acetic acid tert.-butyl ester of the formula

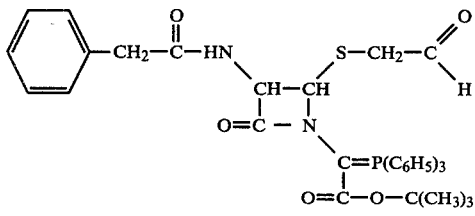

obtained as an intermediate and not isolated, is eluted with a 4:1 mixture of toluene and ethyl acetate and after crystallisation from diethyl ether melts at 149°–151° C.; $[\alpha]_D^{20} = +87°\pm 2°$ (c=0.45 in chloroform); thin layer chromatogram (silica gel): Rf~0.48 (system: toluol-/ethyl acetate, 1:1); ultraviolet absorption spectrum (in pure ethanol): $\lambda_{max}$ 258 mμ; infrared absorption spectrum (in methylene chloride); characteristic bands at 3.00μ, 3.48μ, 5.62μ, 5.81μ, 5.93μ, 6.10μ, 6.67μ, 7.15μ, 7.31μ, 7.70μ, 8.65μ and 9.03μ.

EXAMPLE 2

A mixture of 0.03 g of 7β-(N-phenylacetyl-amino)-ceph-3-em-4-carboxylic acid tert.-butyl ester and 0.5 ml of trifluoroacetic acid is left to stand for one hour at room temperature. The trifluoroacetic acid is then removed under reduced pressure and the residue is twice evaporated to dryness, in each case with 5 ml of a mixture of benzene and chloroform. The residue is chromatographed on 5 g of silica gel and 7β-(N-phenylacetyl-amino)-ceph-3-em-4-carboxylic acid of the formula

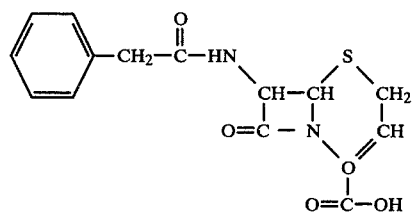

is eluted with methylene chloride, containing 5% of acetone; thin layer chromatogram (silica gel; development with iodine): Rf=0.47 (system: n-butanol/-pyridine/acetic acid/water, 40:24:6:30).

EXAMPLE 3

A mixture of 1.53 g of crude α-[3α-(N-tert.-butoxycarbonyl-D-α-phenylglycyl)-amino-4α-(2-hydroxyethylthio)-2-oxo-1-azetidinyl]-α-(triphenylphosphoranylidene)-acetic acid tert.-butyl ester in 60 ml of a 1:1 mixture of dimethylsulphoxide and acetic anhydride is left to stand for 16 hours at room temperature under a nitrogen atmosphere and is then additionally kept at 50° C. for 2 hours. The mixture is concentrated, the residue is taken up in 500 ml of toluene, and the toluene solution is washed three times with 100 ml of water at a time. The organic phase is dried over sodium sulphate and evaporated. The residue is chromatographed on 120 g of silica gel and 7β-(N-tert.-butoxycarbonyl-D-α-phenylglycyl)-amino-ceph-3-em-4-carboxylic acid tert.-butyl ester of the formula

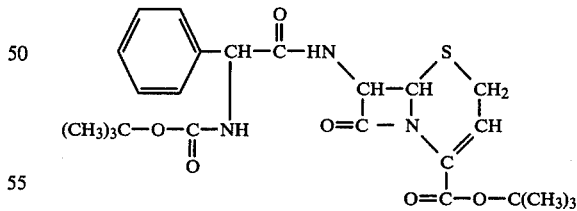

is eluted with an 8:2 mixture of toluene and ethyl acetate. The product crystallises from a mixture of diethyl ether and pentane, melting point 159°–161° C.; $[\alpha]_D^{20} = +29°\pm 2°$ (c=0.521 in chloroform); thin layer chromatography (silica gel; development with iodine vapour): Rf~0.67 (system: toluene/ethyl acetate, 1:1): ultraviolet absorption spectrum (in aethanol):$\lambda_{max}$=255 mμ (ε=5400); infra-red absorption spectrum (in methylene chloride): characteristic bands at 2.68μ, 2.89μ, 3.33μ, 5.57μ, 5.79μ, 5.88μ, 6.08μ, 6.22μ, 6.70μ, 7.15μ, 7.28μ, 7.68μ, 8.04μ, 8.64μ, 9.05μ, 9.52μ and 9.79μ.

EXAMPLE 4

A mixture of 0.6367 g of 7β-(N-tert.-butoxycarbonyl-D-α-phenylglycyl)-amino-ceph-3-em-4-carboxylic acid tert.-butyl ester in 30 ml of trifluoroacetic acid is left to stand for 15 minutes at room temperature and is then treated with 100 ml of toluene and evaporated. The residue is again taken up in 100 ml of a 3:1 mixture of toluene and methanol, the mixture evaporated under reduced pressure, and the residue dried in a high vacuum. The white, pulverulent residue is dissolved in 5 ml of methanol and 13 ml of a 1% strength solution of triethylamine in diethyl ether are added, whereupon a voluminous fresh precipitate forms. The solvent is evaporated off under reduced pressure and the residue is suspended in methylene chloride and filtered off. It is washed with a further 150 ml of methylene chloride and dried in a high vacuum. 7β-(D-α-phenylglycyl)-amino-ceph-3-em-4-carboxylic acid is thus obtained in the zwitter-ion form of the formula

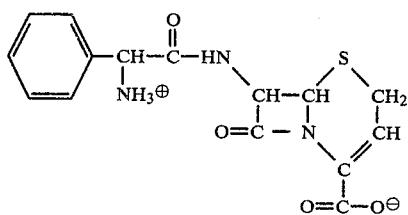

as a pale yellowish, amorphous powder; thin layer chromatogram (silica gel; development with iodine vapour): Rf~0.29 (system: n-butanol/pyridine/acetic acid/water, 40:24:6:30); ultraviolet absorption spectrum (in water): λ$_{max}$=250 mµ (ε=4,300).

EXAMPLE 5

A solution of 0.955 g of 7β-(N-phenylacetyl-amino)-ceph-3-em-4-carboxylic acid in 60 ml of absolute methylene chloride is treated with 0.720 g of trimethylchlorosilane and 0.474 g of absolute pyridine. The mixture is stirred for 60 minutes at room temperature and then cooled to −20° C., and a solution of 3.20 g of absolute pyridine in 30 ml of absolute methylene chloride, and 23.4 ml of an 8% solution of phosphorus pentachloride in absolute methylene chloride, are then added successively. The mixture is stirred for 60 minutes at −10° C. to −12° C. and is again cooled to about −20° C., and 15 ml of absolute methanol are then allowed to run in. The whole is stirred for 25 minutes at −10° C. and then for 35 minutes at room temperature, 15 ml of water are added, the pH value of the reaction mixture is increased from 1.8 to 2.2 by dropwise addition of triethylamine and the mixture is stirred for 20 minutes at room temperature. The pH value is raised to 3.8 by renewed addition of triethylamine and the two-phase mixture is stirred for 90 minutes whilst cooling in an ice bath and is then filtered. The filter residue is washed with methanol, methylene chloride and diethyl ether and is dried in a vacuum desiccator. 7β-amino-ceph-3-em-4-carboxylic acid of the formula

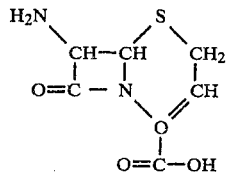

is thus obtained in an amorphous form; the product is further processed without purification.

EXAMPLE 6

A solution of 1.275 g of 7β-phenylacetylamino-ceph-3-em-4-carboxylic acid in 5 ml of methanol and 20 ml of dioxane is treated with an excess of diphenyldiazomethane and allowed to stand at room temperature. The red-coloured reaction mixture is treated with a small amount of acetic acid and then evaporated to dryness under reduced pressure. The oily yellowish residue is taken up in a small amount of methylene chloride, the solution is treated with diethyl ether at an elevated temperature. The colourless precipitate (felt-like needles) is filtered off, washed with diethyl ether, then with pentane and dried to yield the 7β-phenylacetylamino-ceph-3-em-4-carboxylic acid diphenylmethylester of the formula

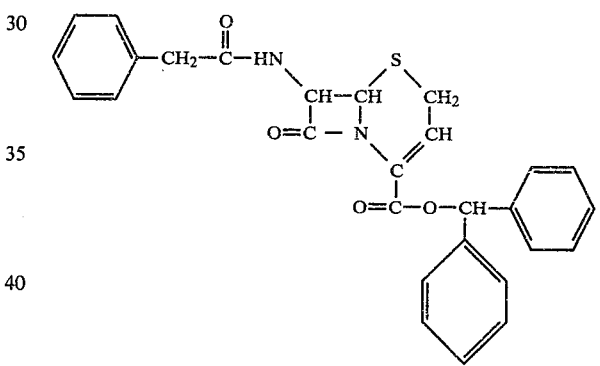

m.p. 163.5°-164.5°; [α]$_D^{20}$=+30°±1° (c=0.968 in dioxane); thin-layer chromatogram (silica gel): Rf=0.55 (system: toluene/acetone 4:1), Rf=0.35 (system: toluene/acetone 9:1) and Rf=0.40 (system: toluene/ethyl acetate 4:1); ultraviolet absorption spectrum: λ$_{max}$=258 mµ (ε=6100) and λ$_{min}$=240 mµ (ε=5250) (in methylene chloride) and λ$_{max}$=259 mµ (ε=6050) and λ$_{min}$=239 mµ (ε=4950); (95% ethanol) infrared absorption spectrum: characteristic bands at 2.90µ, 5.57µ, 5.76µ, 5.91µ, 6.09µ, 6.66µ, 7.13µ, 8.12µ, 8.63µ, 9.07µ, 10.43µ and 12.22µ (in methylene chloride) and at 3.01µ, 5.60µ, 5.82µ, 6.04µ, 6.08µ (shoulder), 6.51µ and 7.13µ (in mineral oil).

The 7β-phenylcaetylamino-ceph-3-em-4-carboxylic acid diphenylmethylester can also be obtained by using in the process of example 1 instead of the α-[4β-(2-hydroxyethylthio)-2-oxo-3β-phenylacetylamino-1-acetidinyl]-α-triphenylphosphoranylidene acetic acid tert.butyl ester the corresponding diphenylmethylester.

A solution of 0.566 g of 7β-phenylacetylamino-ceph-3-em-4-carboxylic acid diphenylmethylester in 2.5 ml of anisole and 10 ml of trifluoroacetic acid is allowed to stand for 20 minutes at room temperature, then several times taken to dryness with toluene until the complete removal of the trifluoroacetic acid. The residue is taken up in ethyl acetate and a 0.5-molar aqueous dipotassium hydrogen phosphate solution.

The layers are separated; the aqueous solution is washed twice with ethyl acetate and the organic solution twice with a 0.5-molar aqueous dipotassium hydrogen phosphate solution. The combined aqueous solution is covered with ethyl acetate and acidified with 20% aqueous phosphoric acid, then extracted with ethyl acetate. The organic extracts are washed with a saturated aqueous sodium chloride solution, dried over magnesium sulfate and evaporated under reduced pressure. The residue is chromatographed on 50 times as much silica gel (washed with concentrated hydrochloric acid); the 7β-phenylacetylamino-ceph-3-em-4-carboxylic acid is eluted with methylene chloride containing 10-20% ethyl acetate. The fractions, which are uniform according to thin-layer chromatography, are crystallized from a mixture of methyl acetate and cyclohexane. The colourless crystals melt at 190°-191° C.; thin-layer chromatogram (silica gel: development with iodine vapor or identification under ultraviolet light): Rf=0.58 (system: n-butanol/acetic acid/water 75:7.5:21), Rf=0.265 (system: n-butanol/ethanol/water 40:10:50), Rf=0.53 (system: n-butanol/acetic acid/water 40:10:40), Rf=0.43 (system: ethyl acetate/pyridine/acetic acid/water 62:21:6:11) and Rf=0.43 (system: ethyl acetate/n-butanol/pyridine/acetic acid/water 42:21:21:6:10).

EXAMPLE 7

A solution of 1.94 g of 7β-phenylacetylamino-ceph-3-em-4-carboxylic acid diphenylmethylester in 100 ml of absolute methylene chloride is cooled to −15°: then treated with 3.86 ml of absolute pyridine and 31.6 ml of an 8% solution of phosphorus pentachloride in methylene chloride; the reaction mixture is stirred for 30 minutes at −10° C. and for another 30 minutes at −5° C. The golden-yellow solution is cooled to −20° C. and 26.8 ml of absolute methanol are added at such a rate that the inner temperature does not exceed −10° C. The reaction mixture is stirred for 1 hour at −10° C., allowed to stand for 1 hour at 25°-30° C. and then treated while stirring vigorously with 80 ml of a 0.5-molar aqueous potassium dihydrogen phosphate solution. The pH-value of the two-phase reaction mixture is adjusted to 2 by adding dropwise 20% aqueous phosphoric acid and stirred for 20 minutes at room temperature. The phases are separated; the aqueous solution is washed twice with methylene chloride. The combined organic solutions are washed with two portions of 20 ml of water each and dried over anhydrous magnesium sulfate. The solvent is evaporated under reduced pressure. The oily residue is placed in a column of 110 g of silica gel, containing 5% water. The phenylacetic acid methyl ester is eluted with methylene chloride and with methylene chloride, containing 3% methyl acetate the 7β-amino-ceph-3-em-4-carboxylic acid diphenyl methyl ester of the formula

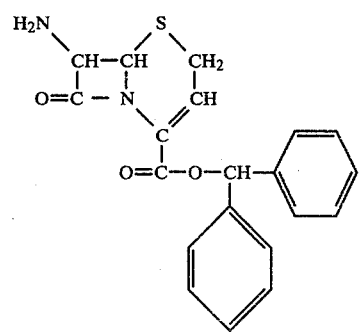

is eluted, crystallized by dissolving it in a small amount of methylene chloride and treating the solution under warming with diethyl ether (needle-like crystals), washed with cold diethyl ether and dried, m.p. 150°-154° C.; thin-layer chromatogram: (silica gel): Rf=0.50 (system: toluene/acetone 4:1), Rf=0.65 (system: toluene/acetone 2:1), Rf=0.40 (system: toluene/ethyl acetate 1:1) and Rf=0.33 (system: toluene/diethyl ether 1:1); ultraviolet absorption spectrum: $\lambda_{max}=257$ mμ ($\epsilon=8150$) and $\lambda_{min}=245$ mμ ($\epsilon=7730$) (in methylene chloride) and $\lambda_{max}=255$ mμ ($\epsilon=5500$) and $\lambda_{min}=236$ mμ ($\epsilon=4650$); (in 95% ethanol) infrared absorption spectrum: characteristic bands at 2.91μ, 2.97μ, 5.61μ, 5.78μ, 6.11μ, 7.14μ, 8.15μ, 8.29μ, 9.14μ and 9.83μ (in methylene chloride) and at 2.99μ, 5.65μ, 5.77μ, 6.08μ, 7.14μ, 7.74μ, 8.08μ, 8.53μ, 9.14μ, 9.85μ and 10.35μ (in mineral oil).

EXAMPLE 8

A total of 0.380 g of 7β-amino-ceph-3-em-4-carboxylic acid diphenylmethyl ester is treated with 2 ml of anisole and 8 ml of absolute trifluoroacetic acid, the clear solution is allowed to stand for 10 minutes at room temperature and then diluted with about 20 ml of absolute toluene. The mixture is evaporated under reduced pressure; the residue is taken twice to dryness with toluene and then suspended in 5 ml of methanol, 5 ml of diethyl ether and 0.5 ml of water. The pH-value of the suspension is adjusted to 3.5 by adding dropwise a 5% solution of triethylamine in methanol; the reaction mixture is allowed to stand for 30 minutes in the ice-bath and the fine precipitate is filtered off with the use of a suitable glass suction filter. The slightly beige-coloured filter residue is washed with a mixture of methanol and methylene chloride, then with diethyl ether and dried at 35° under reduced pressure. The 7β-amino-ceph-3-em-4-carboxylic acid, which is obtained as a fine microcrystalline powder, decomposes at 215° C.; thin-layer chromatogram (silica gel: development with iodine): Rf=0.12 (system: n-butanol/acetic acid/water 67:10:23), Rf=0.28 (system: n-butanol/pyridine/acetic acid/water 40:24:6:30) and Rf=0.21 (system: ethyl acetate/n-butanol/pyridine/acetic acid/water 42:21:21:6:10); infrared absorption spectrum (in mineral oil): characteristic bands at 3.12μ, 3.80μ, 4.12μ (shoulder), 4.92μ, 5.54μ, 6.05μ (shoulder), 6.19μ, 6.55μ, 7.05μ, 7.42μ, 8.23μ, 8.79μ, 9.55μ, 12.08μ, 12.69μ and 13.04μ.

EXAMPLE 9

A suspension of 0.070 g of 7β-amino-ceph-3-em-4-carboxylic acid and 2 ml of absolute methylene chloride is treated with 0.031 g of triethylamine in 0.35 ml of methylene chloride and the suspension is diluted with 5 ml of absolute tetrahydrofurane and stirred for 30 minutes, at times in an ultrasonic bath.

0.102 g of tert.butoxycarbonyl-D-α-phenylglycine is dissolved in 5 ml of absolute methylene chloride, 0.040 g of 4-methylmorpholine is added and the mixture is diluted with 10 ml of acetonitrile. It is cooled to −20° C. and 0.060 g of chloroformic acid isobutyl ester is added whilst stirring, after which the mixture is allowed to react for 30 minutes at −15° C. After renewed cooling to below −20° C., the milky suspension of the triethylammonium salt of 7β-amino-ceph-3-em-4-carboxylic acid is then added. The reaction mixture is stirred for 30 minutes at −15° C., a further 30 minutes at 0° C. and finally for 2 hours at room temperature. The mixture is filtered, the residue is washed with acetonitrile, methylene chloride and diethyl ether, and the filtrate is dried and evaporated to dryness. The residue is taken up in ethyl acetate and water and the mixture is acidified to pH 2 by adding 5 molar aqueous phosphoric acid, whilst vigorously stirring and cooling with ice. The organic phase is separated off and washed four times with small amounts of a saturated aqueous sodium chloride solution. The aqueous extracts are re-extracted with 2 portions of ethyl acetate and the combined organic extracts are dried over anhydrous magnesium sulphate and freed of the solvent under reduced pressure. The residue is chromatographed on 10 g of silica gel (column; 5% water added). Firstly, unreacted tert.-butoxycarbonyl-D-α-phenylglycine is eluted with methylene chloride and with methylene chloride containing increasing proportions of acetone, and subsequently 7β-[N-(N-tert.-butoxycarbonyl-D-α-phenylglycyl)-amino]-ceph-3-em-4-carboxylic acid of the formula

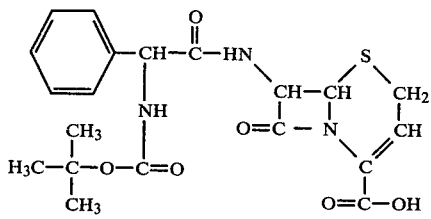

is eluted in the amorphous form; ultraviolet absorption spectrum (in 95% strength ethanol): $\lambda_{max}=252$ mμ ($\epsilon=5100$); infra-red absorption spectrum (in methylene chloride): characteristic bands at 5.61μ, 5.85μ, 5.92μ and 6.12μ; thin layer chromatogram (silica gel G; detection with iodine vapour): Rf=0.6–0.7 (system: n-butanol/acetic acid/water, 44:12:44).

EXAMPLE 10

A solution of 0.02 g of 7β-[N-(N-tert.-butoxycarbonyl-D-α-phenylglycyl)-amino]-ceph-3-em-4-carboxylic acid in 3 ml of pure trifluoroacetic acid is left to stand for 15 minutes at room temperature. The resulting solution is evaporated in a rotary evaporator and the residue is twice evaporated to dryness, in each case with 20 ml of a 1:1 mixture of chloroform and toluene, in order to remove the trifluoroacetic acid completely, and is dried for 16 hours at 0.0001 mm Hg. 7β-[N-(D-α-phenylglycyl)-amino]-ceph-3-em-4-carboxylic acid is obtained as a yellowish powder by treating a solution, in water and methanol, of the resulting salt with trifluoroacetic acid with an equivalent amount of triethylamine, evaporating, and digesting the residue with methylene chloride. The product is identical, according to thin layer chromatography and spectroscopically, to the product described in Example 4.

EXAMPLE 11

A suspension of 0.20 g of N-(2,2,2-trichloroethoxycarbonyl)-D-α-phenylglycine in 6 ml of a 1:1 mixture of tetrahydrofurane and acetonitrile is treated with 0.085 ml of triethylamine. After cooling to −10° C., 0.08 ml of chloroformic acid isobutyl ester is added with exclusion of moisture, and the mixture is stirred for 15 minutes at −10° C. A solution consisting of 0.160 g of 7β-amino-ceph-3-em-4-carboxylic acid and 0.081 ml of triethylamine in 2 ml of a 1:1 mixture of water and tetrahydrofurane is added dropwise to the solution of the mixed anhydride in such a way that the internal temperature does not rise above 0° C. The reaction mixture is stirred for a further 30 minutes at 0° C. and for 90 minutes at room temperature and the bulk of the organic solvent is then evaporated under reduced pressure. The residue is diluted with 5 ml of an 0.5 molar aqueous dipotassium hydrogen phosphate solution and with 5 ml of ethyl acetate. Undissolved material is filtered off by means of a glass suction filter and a diatomaceous earth preparation. The layers of the filtrate are separated; The organic phase is re-extracted with the dipotassium hydrogen phosphate solution, and discarded. The aqueous phases are washed with ethyl acetate, covered with fresh ethyl acetate and acidified to pH 2 with concentrated phosphoric acid. The organic phase is separated off and repeatedly washed with a saturated aqueous sodium chloride solution. The aqueous phases are twice reextracted with 10 ml of ethyl acetate at a time, and discarded. The combined organic extracts are dried over sodium sulphate, and freed of the solvent under reduced pressure. The crude product is chromatographed on 10 g of silica gel. Unchanged N-(2,2,2-trichloroethoxy-carbonyl)-D-α-phenylglycine is eluted with a 4:1 mixture of toluene/ethyl acetate. 7β-[N-(2,2,2-trichloroethoxycarbonyl)-D-α-glycyl]-amino-ceph-3-em-4-carboxylic acid of the formula

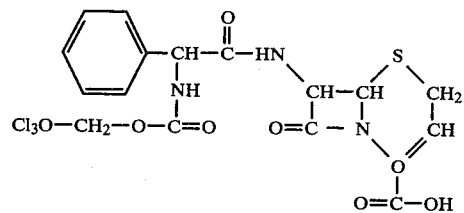

is eluted with a toluene-ethyl acetate mixture, using increasing proportions of ethyl acetate relative to the 4:1 ratio; infra-red absorption spectrum (in mineral oil): characteristic bands 5.61μ, 5.86μ, 5.92μ and 6.12μ; ultraviolet absorption spectrum (in ethanol): $\lambda_{max}=252$ mμ; thin layer chromatogram (silica gel; development with iodine vapour): Rf ~0.8 (system: n-butanol/acetic acid/water, 71.5:7.5:21).

EXAMPLE 12

A solution of 0.120 g of 7β-[N-(2,2,2-trichloroethoxycarbonyl)-D-α-phenylglycyl]-amino-ceph-3-em-4-carboxylic acid in 6 ml dimethylformamide is mixed with 10 ml of 90% strength acetic acid and then treated with 0.600 g of zinc dust. The mixture is stirred for 1 hour at room temperature, the unreacted zinc dust is filtered off and rinsed with dimethylformamide, and the filtrate is stirred for about 10 minutes with 25 ml of an ion exchanger (Dowex 50-16; 20–50 mesh; sulphonic acid type, in the H-ion form). The exchanger is filtered off and washed with water. The filtrate is evaporated to dryness in a high vacuum at a bath temperature of below 30° C. (rotary evaporator). The residue is dissolved in 5 ml of an 8:2 mixture of methanol and water and adjusted to pH 4.3 with a 1% strength solution of triethylamine in methanol. The whole is stirred for 1 hour in an ice bath and evaporated to dryness, and the residue is digested with methylene chloride. The product is filtered off, thoroughly washed with methylene chloride and dried in a high vacuum. 7β-(D-α-phenylglycylamino)-ceph-3-em-4-carboxylic acid is thus obtained, which is identical to the compound obtainable according to the process of Example 4.

EXAMPLE 13

The 7β-amino-ceph-3-em-4-carboxylic acid described in Example 5 or 7 can be N-acylated and converted into 7β-(N-acylamino)-ceph-3-em-4-carboxylic acids of the formula

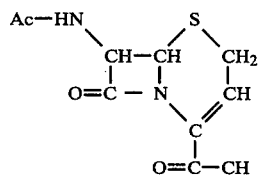
(IB)

in accordance with the following general processes:

Variant A: 0.4 mmol of an acid [AcOH] is dissolved in 4 ml of absolute methylene chloride with the addition of 0.056 ml (0.4 mmol) of triethylamine [stock solution: 28.0 ml (200 mmols) of triethylamine, diluted to 100 ml with methylene chloride]. 0.0452 ml (0.4 mmols) of trichloroacetic acid chloride in 0.2 ml of methylene chloride [stock solution 22.6 ml (200 mmols) of trichloroacetic acid chloride diluted with methylene chloride to 100 ml] is added to the solution cooled to −15° C. and the mixture is stirred for 30 minutes at −15° C. The solution containing the mixed anhydride [Ac-O-C(=O)-CCl₃] is mixed with a finely dispersed suspension, cooled to −15° C., of 0.040 g (0.2 mmol) of 7β-amino-ceph-3-em-4-carboxylic acid and 0.056 ml (0.4 mmol) of triethylamine in 4 ml of methylene chloride, and the mixture is vibrated in an ultrasonics bath for 30 minutes at −15° C. and then for 30 minutes at 20° C. The reaction solution, which is usually brown, is evaporated to dryness under reduced pressure, and the resulting residue is distributed between 10 ml of a 10% strength aqueous dipotassium hydrogen phosphate solution (pH 8.9) and 5 ml of ethyl acetate. The aqueous phase is adjusted to pH 2.6 with 20% strength aqueous phosphoric acid and thereupon exhaustively extracted with ethyl acetate. The ethyl acetate extract (30–50 ml) is washed with water, dried over sodium sulphate and evaporated under reduced pressure. The residue is preparatively chromatographed in a suitable solvent system for 2–5 hours on a thin layer plate of silica gel. After drying the plate at room temperature in a nitrogen atmosphere, the silica gel zone which absorbs under ultraviolet light (254 mμ) is mechanically detached from the plate and extracted three times with 10 to 30 ml of ethanol or methanol. After evaporation of the extract under reduced pressure, 7β-N-Acamino-ceph-3-em-4-carboxylic acid is obtained as a beige or almost colourless residue.

If the thin layer plate displays more than one zone which absorbs in the ultraviolet light, the individual zones are separately worked up as described above. A sample of the material resulting frowm the various zones is tested in the plate diffusion test against *Straphylococcus aureus*. The material from the zone which is microbiologically the most active is subjected to a renewed preparative thin layer separation, whereby the product which is chromatographically a single substance can be isolated.

Variant B: 0.2 mmol of the sodium salt of an acid [AcONa] in 2 ml of absolute dimethylformamide is mixed with 0.2 mmol of trichloroacetyl chloride as in Variant A, reacted with a solution of 0.2 mmol of 7β-amino-ceph-3-em-4-carboxylic acid and 0.2 mmol of triethylamine in 0.2 ml of dimethylformamide, as in Variant A, and worked up.

Variant C: A mixture of 0.25 mmol of an acid chloride [AcCl] in 2 ml of methylene chloride is added to a solution, cooled to −15° C. of 0.040 mg (0.2 mmol) of 7β-amino-ceph-3-em-4-carboxylic acid and 0.070 ml (0.5 mmol) of triethylamine in 5 ml of methylene chloride and reacted and worked up as in Variant A.

EXAMPLE 14

If in the process of Example 13, Variant B, the sodium salt of malonic acid methyl half-ester is used as the acylating starting material, 7β-(N-methoxy-carbonylacetylamino)-ceph-3-em-4-carboxylic acid of the formula IB is obtained, wherein Ac denotes the radical of the formula

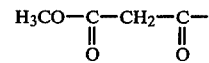

this compound showing an Rf value of 0.5–0.6 in a thin layer chromatogram (silica gel; system ethyl acetate/acetic acid, 9:1); ultraviolet absorption spectrum (in methanol): $\lambda_{max}$ at 255 mμ; infrared absorption spectrum (in mineral oil): characteristic bands at 5.58μ.

EXAMPLE 15

If in the process of Example 13, Variant A, bromoacetic acid chloride is used as the acylating starting material, 7β-(N-bromoacetyl-amino)-ceph-3-em-4-carboxylic acid of the formula IB, wherein Ac denotes the radical of the formula

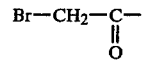

is obtained, this substance showing an Rf-value of 0.25–0.35 in a thin layer chromatogram (silica gel; system n-butanol/acetic acid/water, 75:7.5:21); ultraviolet absorption spectrum (0.1 molar aqueous sodium hydrogen carbonate solution): $\lambda_{max}$ at 254 mμ.

EXAMPLE 16

A mixture of 0.128 g (0.4 mmol) of 7β-(N-bromoacetylamino)-ceph-3-em-4-carboxylic acid in 0.5 ml of methanol and 0.047 g (0.5 mmol) of 4-amino-pyridine is reacted in the presence of 0.048 g (0.5 mmol) of diisopropyl-ethylamine at 40° C. until the reaction is complete (checked by means of thin layer chromatography). The mixture is evaporated and the residue is twice subjected to preparative thin layer chromatography (silica gel). The 7β-[N-(4-aminopyridiniumacetyl)-amino]-ceph-3-em-4-carboxylic acid of the formula

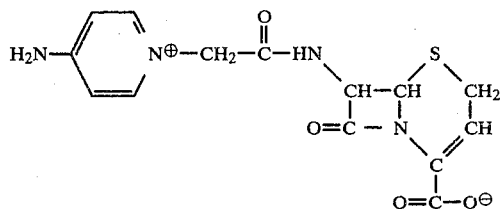

obtainable in this way shows an Rf-value of 0.25–0.4 in a thin layer chromatogram (silica gel; system n-butanol/pyridine/acetic acid/water, 42:24:4:30); ultraviolet absorption spectrum (in water); $\lambda_{max}$ at 262 mμ; infrared absorption spectrum (in mineral oil): characteristic band at 5.62μ.

EXAMPLE 17

If in Example 13, Variant C, phenyloxyacetyl chloride is used as the acylating starting material, 7β-(N-phenyloxyacetyl-amino)-ceph-3-em-4-carboxylic acid of the formula IB, wherein Ac denotes the radical of the formula

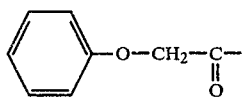

is obtained, this substance showing an Rf-value of 0.4–0.5 in a thin layer chromatogram (silica gel; system n-butanol/acetic acid/water, 75:7.5:21).

EXAMPLE 18

A mixture of 0.160 g of 7β-(N-bromoacetyl-amino)-ceph-3-em-4-carboxylic acid, 0.066 g of 4-mercaptopyridine and 0.57 g of diisopropylethylamine in 5 ml of dimethylformamide is allowed to react for 4 hours at room temperature. The mixture is evaporated, the residue is digested with a 1:1 mixture of acetone and diethyl ether, and the product is filtered off and thoroughly rinsed. 7β-[N-(4-pyridylthioacetyl)-amino]-ceph-3-em-4-carboxylic acid of the formula IB, wherein Ac denotes the radical of the formula

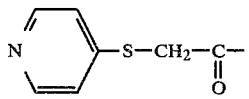

and which is obtainable in the amorphous form, shows an Rf value of 0.35–0.45 in a thin layer chromatogram (silica gel; system n-butanol/pyridine/acetic acid/water, 42:24:4:30); infrared absorption spectrum (in mineral oil): characteristic bands at 5.62μ.

EXAMPLE 19

A 10% strength suspension of 0.040 g of 7β-amino-ceph-3-em-4-carboxylic acid and 0.0202 g (0.2 mmol) of triethylamine in methylene chloride is mixed with a 10% strength solution of 0.0218 g (0.26 mmol) of diketene in methylene chloride and the mixture is vibrated for one hour at 22° C. in an ultrasonics bath; after about 30 minutes a clear solution is obtained. The reaction mixture is worked up in accordance with the process of Example 13, Variant A, and 7β-(N-acetoacetyl-amino)-ceph-3-em-4-carboxylic acid of the formula IB, wherein Ac denotes the radical of the formula

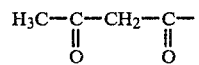

is thus obtained, this substance showing an Rf-value of 0.3–0.4 in a thin layer chromatogram (silica gel; system n-butanol/acetic acid/water, 75/7.5:21); ultraviolet absorption spectrum (in an 0.1 M aqueous sodium hydrogen carbonate solution); $\lambda_{max}$ at 238 mμ and 265 mμ

EXAMPLE 20

If in the process of Example 13, Variant A, cyanoacetic acid is used as the acylating starting material, 7β-(N-cyanoacetyl-amino)-ceph-3-em-4-carboxylic acid of the formula IB, wherein Ac denotes the radical of the formula

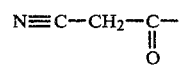

is obtained, this substance showing an Rf-value of 0.45–0.55 in a thin layer chromatogram (silica gel; system n-butanol/pyridine/acetic acid/water, 38:24:8:30); ultraviolet absorption spectrum (in 0.1 molar aqueous sodium hydrogen carbonate solution); $\lambda_{max}$ at 254 mμ; infrared absorption spectrum (in mineral oil): characteristic bands at 4.32μ and 5.60μ.

EXAMPLE 21

If in Example 13, Variant C, α-cyanopropionic acid chloride is used as the acylating starting material, 7β-(N-α-cyanopropionyl-amino)-ceph-3-em-4-carboxylic acid of the formula IB, wherein Ac denotes the radical of the formula

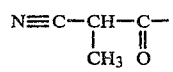

is obtained, this substance showing an Rf-value of 0.5–0.6 in a thin layer chromatogram, (silica gel; system n-butanol/pyridine/acetic acid/water, 38:24:8:30); ultraviolet absorption spectrum (in 0.1 molar aqueous sodium hydrogen carbonate solution): $\lambda_{max}$ at 255 mμ; infrared absorption spectrum (in mineral oil): characteristic bands at 4.44μ and 5.62μ.

EXAMPLE 22

If in the process of Example 13, Variant A, α-cyanophenylacetic acid is used as the acrylating starting material, 7β-(N-α-cyanophenylacetyl-amino)-ceph-3-em-4-carboxylic acid of the formula IB, wherein Ac denotes the radical of the formula

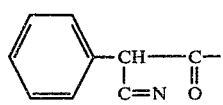

is obtained, this substance showing an Rf-value of 0.3–0.4 in a thin layer chromatogram (silica gel; system n-butanol/acetic acid/water, 75:7.5:21); ultraviolet absorption spectrum (in 0.1 molar aqueous sodium hydrogen carbonate solution): $\lambda_{max}$ at 260 mμ; infrared absorption spectrum (in mineral oil): characteristic bands at 4.42μ and 5.62μ.

EXAMPLE 23

A 10% strength suspension of 0.040 g (0.2 mmol) of 7-amino-ceph-3-em-4-carboxylic acid and 0.0429 g (0.3 mmol) of tri-n-butylamine in dimethylformamide is mixed with a 10% strength solution of 0.0422 g (0.4 mmol) of 2-chloroethylisocyanate in dimethylformamide, and the mixture is vibrated for one hour at 22° C. in an ultrasonics bath. It is then worked up in accordance with the process described in Example 13, Variant A, and 7β-[N-(2-chloroethyl-aminocarbonyl)-amino]ceph-3-em-4-carboxylic acid of the formula IB, wherein Ac denotes the radical of the formula

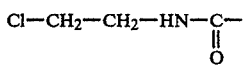

is thus obtained, this substance showing Rf-values of 0.4–0.5 (system n-butanol/acetic acid/water, 75:7.5:21) in a thin layer chromatogram (silica gel)l ultraviolet absorption spectrum (in 0.1 molar aqueous sodium hydrogen carbonate solution): $\lambda_{max}$ at 254 mμ.

EXAMPLE 24

If in the process of Example 13, Variant A, dichloroacetic acid is used as the acylating starting material, 7β-(N-dichloroacetyl-amino)-ceph-3-em-4-carboxylic acid of the formula IB, wherein Ac denotes the radical of the formula

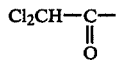

is obtained, this substance showing an Rf-value of 0.50 in a thin layer chromatogram (silica gel; system n-butanol/acetic acid/water, 75:7.5:21); ultraviolet absorption spectrum (in 0.1 molar aqueous sodium hydrogen carbonate solution): $\lambda_{max}$ at 253mμ; infrared absorption spectrum (in mineral oil): characteristic band at 5.67μ.

EXAMPLE 25

If in Example 13, Variant C, phenylacetic acid chloride is used as the acylating starting material, 7β-(N-phenylacetyl-amino)-ceph-3-em-4-carboxylic acid of the formula IB, wherein Ac denotes the radical of the formula

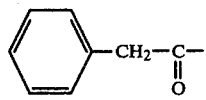

is obtained with this substance showing an Rf-value of 0.47 in a thin layer chromatogram (silica gel; system n-butanol/pyridine/acetic acid/water, 40:24:6:30). According to a thin layer chromatogram, the compound is identical with the compound which can be manufactured according to the process described in Example 2.

EXAMPLE 26

If in Example 13, Variant C, 2-thienylacetyl chloride is used as the acylating starting material, 7β-(N-2-thienylacetyl-amino)-ceph-3-em-4-carboxylic acid of the formula IB, wherein Ac denotes the radical of the formula

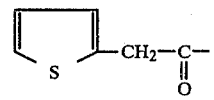

is obtained, with this substance showing an Rf-value of 0.5–0.6 in a thin layer chromatogram (silica gel; system n-butanol/pyridine/acetic acid/water, 38:24:8:30); ultraviolet absorption spectrum (in 0.1 molar aqueous sodium hydrogen carbonate solution): $\lambda_{max}$ at 237 mμ; infrared absorption spectrum (in mineral oil): characteristic band at 5.62μ.

EXAMPLE 27

If in the process of Example 13, Variant A, phenylmalonic acid is used as the acylating starting material, 7β-(N-α-carboxyl-phenylacetyl-amino)-ceph-3-em-4-carboxylic acid of the formula IB, wherein Ac denotes the radical of the formula

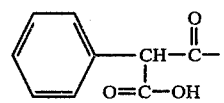

is obtained, this substance showing two zones in a thin layer chromatogram (silica gel; system n-butanol/pyridine/acetic acid/water, 40:24:6:30) the more rapidly migrating zone, with Rf=0.45, contains 7β-(N-phenylacetyl-amino)-ceph-3-em-4-carboxylic acid and the more slowly migrating zone with Rf=0.2–0.3 contains the desired 7β-(N-α-carboxy-phenylacetyl-amino)-ceph-3-em-4-carboxylic acid.

EXAMPLE 28

If in the process of Example 13, Variant B, the sodium salt of DL-α-(N-tert.-butoxycarbonyl-amino)-2-thienylacetic acid is used as the acylating starting material, 7β-[N-α-(N-tert.-butoxycarbonyl-amino)-2-thienylacetyl-amino]ceph-3-em-4-carboxylic acid of the formula IB, wherein Ac denotes the radical of the formula

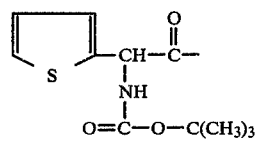

is obtained; this substance is purified by thin layer chromatography (silica gel) and shows an RF-value of 0.5–0.6 in the system acetic acid ethyl ester/pyridine/acetic acid/water (62:21:6:11). It can be converted in accordance with the process described in Example 4 into 7β-[N-(α-amino-2-thienylacetyl)-amino]-ceph-3- em-4-carboxylic acid of the formula IB, wherein Ac denotes the radical of the formula

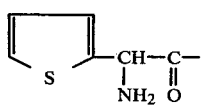

this is present as a zwitter-ion and shows an Rf-value of 0.4–0.5 in a thin layer chromatogram (silica gel) in the system ethyl acetate/methyl ethyl ketone/formic acid/water (50:30:10:10).

EXAMPLE 29

A solution of the 7β-(N-bromoacetyl-amino)-ceph-3-em-4-carboxylic acid obtainable according to the process described in Example 15 (about 0.15 mmol) in 0.3 ml of a solution of 17.3 ml of diisopropyl-ethylamine in 100 ml of methylene chloride is mixed with 0.0126 g (0.18 mmol) of tetrazole in 0.3 ml of dimethylformamide and allowed to react for 30 minutes at room temperature. The mixture is worked up according to the process described in Example 13 and 7β-(N-1-tetrazolylacetyl-amino)-ceph-3-em-4-carboxylic acid of the formula IB, wherein Ac denotes the radical of the formula

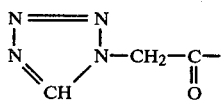

is thus obtained, this substance showing an Rf-value of 0.4–0.5 in a thin layer chromatogram (silica gel; system n-butanol/pyridine/acetic acid/water (42:24:4:30); ultraviolet absorption spectrum (in methanol): $\lambda_{max}$ at 255 mμ.

EXAMPLE 30

If a solution of the 7β-(N-bromoacetyl-amino)-ceph-3-em-4-carboxylic acid obtainable according to the process described in Example 15 (about 0.15 mmol) in 0.3 of a solution of 17.3 ml of diisopropyl-ethylamine in 100 ml of methylene chloride is reacted with 0.0205 g (0.18 mmol) of 2-mercapto-1-methyl-imidazole in 0.3 ml of dimethylformamide according to the process described in Example 29 the mixture being allowed to react for 7 hours at 20° C., 7β-[N-(1-methyl-2-imidazolyl-thioacetyl)-amino]-ceph-3-em-4-carboxylic acid of the formula IB, wherein Ac denotes the radical of the formula

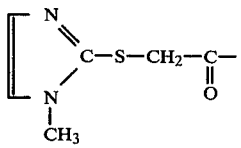

is obtained, this substance showing an Rf-value of 0.3–0.4 in a thin layer chromatogram (silica gel; system n-butanol/pyridine/acetic acid/water (42:24:4:30); ultraviolet absorption spectrum (in methanol): $\lambda_{max}$ at 252 mμ.

EXAMPLE 31

A solution of 0.037 g of sodium nitrite in 0.4 ml of water is added to a cooled and stirred solution of 0.100 g of 4-guanylsemicarbazide dihydrochloride in 0.6 ml of water. The mixture is stirred for 10 minutes at 0° C. and is then added dropwise at 0° to a solution of 0.173 g of 7β-[N-(D-α-phenylglycyl)-amino]-ceph-3-em-4-carboxylic acid in 4 ml of water which has been adjusted to pH 7.5 with triethylamine. The mixture is stirred for 1 hour at 0° C. and the precipitate which has separated out is filtered off, washed with water and dried. Crude 7β-[N-D-α-(3-guanyl-ureido)-phenylacetylamino]-ceph-3-em-4-carboxylic acid of the formula IB, wherein Ac denotes the radical of the formula

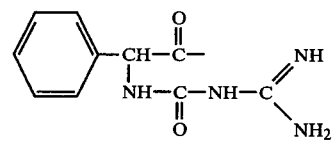

is thus obtained; in a thin layer chromatogram (silica gel; development with iodine vapour): Rf~0.30–0.35 (system: n-butanol/acetic acid/water, 67:10:23); ultraviolet absorption spectrum (in methanol): $\lambda_{max}$=252 mμ.

EXAMPLE 32

On using 7β-[N-(D-α-amino-2-thienylacetyl)-amino]-ceph-3-em-4-carboxylic acid and following the procedure of Example 31, 7β-[N-D-α-(3-guanyl-ureido)-2-thienylacetylamino]-ceph-3-em-4-carboxylic acid of the formula IB, wherein Ac denotes the radical of the formula

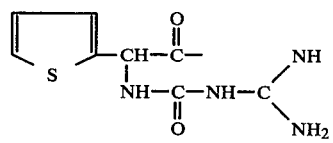

is obtained as an amorphous powder.

EXAMPLE 33

A suspension of 0.100 g of 7β-[N-(D-α-phenylglycyl)amino]-ceph-3-em-4-carboxylic acid in 5 ml of absolute methylene chloride is treated with 0.0364 g of triethylamine and stirred for 10 minutes; thereupon most of the material dissolves. The mixture is cooled to −5° C. and a total of 0.0652 g of the triethylamine-sulphur trioxide complex (melting point 89°–90° C.) is added in portions. The mixture is stirred for 5 minutes at 0° C. and for two hours at 20° C. The solution is treated with 0.9 mmol of sodium α-ethyl-hexanoate and the product which has separated out is filtered off. After washing with methylene chloride and diethyl ether, the pulverulent precipitate, containing the disodium salt of 7β-[N-(D-α-sulphoamino-phenylacetyl)-amino]-ceph-3-em-4-carboxylic acid of the formula IB, wherein Ac denotes the radical of the formula

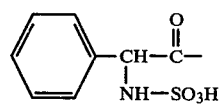

is dried under a high vacuum; thin layer chromatogram (silica gel): Rf=0.10 (system: n-butanol/acetic acid/water 71.5:7.5:21); ultraviolet absorption spectrum (in water): $\lambda_{max}=253$ m$\mu$.

EXAMPLE 34

On using 7β-[N-(D-α-amino-2-thienylacetyl)-amino]-ceph-3-em-4-carboxylic acid in Example 33, the disodium salt of 7β-[N-(D-α-sulphonamino-2-thienylacetyl)-amino]-ceph-3-em-4-carboxylic acid of the formula IB, wherein Ac denotes the radical of the formula

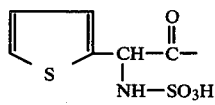

is obtained analogously an an amorphous powder.

EXAMPLE 35

A suspension of 0.110 g of 7β-amino-ceph-3-em-4-caboxylic acid in 2 ml of water is dissolved by adding 0.0635 g of sodium bicarbonate and 0.142 g of α-sulphophenylacetyl chloride in 3 ml of diethyl ether is added dropwise at 0° C. The mixture is stirred for 1 hour at 0°-5° C. and subsequently treated with 1.5 mmols of sodium α-ethyl-hexanoate, and the product which has separated out is filtered off. After washing with methylene chloride and diethyl ether the pulverulent precipitate, consiting of the disodium salt of 7β-[N-(α-sulphophenylacetyl)-amino]-ceph-3-em-4-carboxylic acid of the formula IB, wherein Ac denotes the radical of the formula

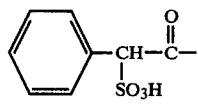

is dried under a high vacuum; thin-layer chromatogram (silica gel): Rf~0.15-0.25 (system: n-butanol/acetic acid/water, 67:10:23).

EXAMPLE 36

A total of 0.335 g of 7β-(D-α-phenylglycyl)-amino-ceph-3-em-4-carboxylic acid is dissolved at 5° in 15 ml of water, treated with 0.085 g of sodium hydrogen carbonate, which is followed by 0.030 g of formaldehyde. The mixture is stirred for 2 hours, filtered and the filtrate is lyophilized. The residue represents 7β-(5-oxo-4-phenyl-1,3-diaza-1-cyclopentyl)-ceph-3-em-4-carboxylic acid of the formula

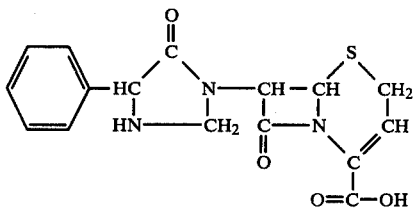

which in the thin-layer chromatogram (silica gel) has an Rf-value of 0.25 (system: n-butanol/pyridine/acetic acid/water 40:24:6:30).

EXAMPLE 37

A mixture of 1.0 g of 7β-(D-α-phenylglycyl)-amino-ceph-3-em-4-carboxylic acid in 10 ml of acetone is treated with 0.8 ml of triethylamine. The reaction mixture is stirred for 24 hours at room temperature, filtered and the filtrate is evaporated. The residue is dissolved in water, the pH-value is adjusted to 2.5 with 2 N hydrochloric acid, and the precipitate is then filtered off and dried. The 7β-(2,2-dimethyl-5-oxo-4-phenyl-1,3-diazacyclopentyl)-ceph-3-em-4-carboxylic acid of the formula

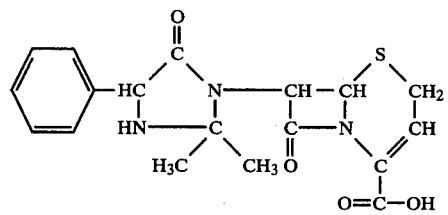

is obtained as a colourless product; thin-layer chromatogram (silica gel): Rf=0.40 (system: n-butanol/pyridine/acetic acid/water 40:24:6:30).

The starting substances used in the preceding examples can be manufactured as follows:

A. 15 ml of a sulphonic acid type of ion exchanger (H⊕-form) are converted into the triethylammonium salt form by treatment with a solution of 5 ml of triethylamine in 100 ml of water, and the column is washed with 300 ml of water until neutral, treated with a solution of 2 g of the sodium salt of penicillin-G in 10 ml of water, and thereafter eluted with water. A volume of 45 ml is withdrawn and lyophilised at a pressure of 0.01 mm Hg. The crude triethylammonium salt of penicillin-G thus obtained is dissolved in methylene chloride, and the solution is dried over sodium sulphate, filtered and evaporated.

A solution of the penicillin-G-triethylammonium salt thus obtainable, in a mixture of 40 ml of methylene chloride and 40 ml of tetrahydrofurane, is cooled to −10° C. and 2.9 ml of a 10 ml solution of 2 ml of chloroformic acid ethyl ester in tetrahydrofurane is slowly added whilst stirring. The mixture is stirred for 90 minutes at −5° C. to 0° C., a solution of 0.395 g of sodium azide in 4 ml of water is then added, and the mixture is stirred for 30 minutes at −5° C. to 0° C. It is diluted with 100 ml of ice water and extracted three times with 75 ml portions of methylene chloride; the organic extracts are washed with water, dried and evaporated at room temperature under reduced pressure. The amorphous penicillin-G-azide is thus obtained, infrared absorption spectrum (in methylene chloride): characteristic bands at 3.05$\mu$, 4.71$\mu$, 5.62$\mu$, 5.80$\mu$, 5.94$\mu$, 6.69$\mu$ and 8.50$\mu$.

A solution of 1.72 g of the penicillin-G-azide in 30 ml of benzene is mixed with 1.5 ml of 2,2,2-trichloroethanol and stirred for 25 hours at 70° C. During the first 15 minutes, a uniform evolution of nitrogen is observed and after some hours the product separates out from the solution. The mixture is diluted with 60 ml of hexane whilst stirring, cooled and filtered after 15 minutes. The filter residue is washed with a 2:1 mixture of benzene and hexane and with cold ether. Pure 2,2-dimethyl-6β-(N-phenylacetyl-amino)-3-(N-2,2,2-trichloroethoxycarbonylamino)-penam is thus obtained, melting at 223°–223.5° C.; $[\alpha]_D^{20} = +172°$ (c=1.018 in ethanol); infrared absorption spectrum (in methylene chloride): characteristic bands at 3.04μ, 5.61μ, 5.77μ, 6.97μ, 6.70μ, 8.30μ, 9.17μ, 9.62μ and 11.85μ.

The product can also be obtained by warming 0.03 g of the penicillin-G-azide in 2 ml of benzene to 70° C. for 20 minutes, obtaining the 3-isocyanato-2,2-dimethyl-6β-(N-phenylacetyl-amino)-penam [infrared absorption spectrum (in methylene chloride): characteristic bands at 3.06μ, 4.48μ, 5.62μ, 5.96μ and 6.70μ] by evaporation of the reaction mixture under reduced pressure, and converting this, by reaction with 2,2,2-trichloroethanol, into the desired 2,2-dimethyl-6β-(N-phenylacetylamino)-3-(N-2,2,2-trichloroethoxycarbonyl-amino)-penam.

A solution of 11.0 g of 2,2-dimethyl-6γ-(N-phenylacetyl-amino)-3-(N-2,2,2-trichloroethoxycarbonyl-amino)-penam in a mixture of 240 ml of anhydrous methylene chloride and 25.6 ml of pyridine is treated with 166 ml of a 10% strength solution of phosphorus pentachloride in methylene chloride under a nitrogen atmosphere −10° C., and is subsequently stirred for 30 minutes at 0° C. 120 ml of absolute methanol are then added whilst cooling strongly (−10° C.) and the mixture is stirred for a further 2 hours. 80 ml of water are added, the pH value (measured in samples diluted with water) is adjusted to 3.3 with about 9 ml of a 2 N aqueous sodium hydroxide solution, and the reaction is allowed to continue for an hour at 0° C. and a further hour at 20° C. The mixture is then poured out into 500 ml of a 1 M aqueous dipotassium hydrogen phosphate buffer solution whilst stirring, and the pH value is adjusted from 6.5 to 7.0 by adding 50% strength aqueous tripotassium phosphate solution. The aqueous phase is separated off and twice washed with 200 ml of methylene chloride at a time; the three organic solutions are each twice washed with water, combined, dried over sodium sulphate and evaporated under reduced pressure. The crystalline residue is taken up in 40 ml of a 1:1 mixture of benzene and hexane; the mixture is cooled for 15 minutes at 0° C. and the precipitate is filtered off. 6β-Amino-2,2-dimethyl-3-(N-2,2,2-trichloroethoxycarbonyl-amino)-penam is thus obtained, melting at 179°–180° C. (corrected); infrared absorption spectrum: characteristic bands (in methylene chloride) at 2.90μ, 5.58μ, 6.62μ, 7.17μ, 7.27μ, 8.32μ, 8.46μ, 8.82μ, 9.25μ, and 9.62μ; (in Nujol) at 2.95μ, 3.01μ, 3.11μ, 5.64μ, 5.80μ, 6.35μ, 7.60μ, 7.87μ, 8.00μ, 8.27μ, 8.65μ, 8.70μ, 9.16μ, and 9.57μ; thin layer chromatogram (silica gel): Rf=0.17 (in the system toluene/acetone, 8:2) and Rf=0.43 (in the system toluene/acetone, 6:4); characteristic yellow colouration with ninhydrine-collidine (free amino group).

A mixture of 0.05 g of 6β-amino-2,2-dimethyl-3-(N-2,2,2-trichloroethoxycarbonyl-amino)-penam and 0.1 g of zinc dust in 2 ml of a 1:1 mixture of acetone and water is treated with 0.2 ml of acetic acid and then vibrated for one hour at 20° C. with 45 kHz (ultrasonics) and thereafter diluted with 50 ml of water. This mixture is extracted with 50 ml of ethyl acetate and the organic extract is dried over sodium sulphate and evaporated under reduced pressure. The residue is recrystallised from a mixture of methylene chloride and hexane, and 3-isopropyl-4-thia-2,6-diazabicyclo[3.2.0]heptan-7-one, melting point 151°–155° C., is thus obtained; thin layer chromatogram: Rf=0.17 (system: toluene/acetone 8:2) and Rf=0.38 (system: toluene/acetone, 6:4).

Instead of acetic acid, 0.2 g of ammonium chloride or 0.2 g of pyridine hydrochloride can be used in the above process.

A solution of 1.64 g of 3-isopropyl-4-thia-2,6-diazabicyclo[3.2.0]heptan-7-one in 33 ml of a 1:1 mixture of acetic acid and water is treated over the course of 10 minutes with 71.7 ml of an 0.5 N solution of iodine in ethanol and the mixture is left to stand for one hour at room temperature and is then concentrated under reduced pressure. The residue is dried in a high vacuum, suspended in 90 ml of acetonitrile, and treated with 4.5 ml of pyridine and 4.5 ml of phenylacetic acid chloride at 0° C. The whole is left to stand for 15 minutes at 0° C. for one hour at room temperature and is then evaporated under reduced pressure. The product is triturated for 30 minutes with 10 ml of a 1:1 mixture of dioxane and water, and the residue is taken up in ethyl acetate; the solution is washed with a saturated aqueous sodium bicarbonate solution and a saturated aqueous sodium chloride solution, dried and evaporated. The oily residue is chromatographed on 100 g of pure silica gel; the oily bis-[cis-2-oxo-3β-(N-phenylacetyl-amino)-4β-azetidinyl]-disulphide is eluted with a 19:1 mixture of ethyl acetate and acetone and is converted into a finely powdered amorphus form by lyophilisation; thin layer chromatogram (silica gel): Rf ~0.36 (system: ethyl acetate/acetone, 1:1); infrared absorption spectrum (in potassium bromide): characteristic bands at 3.08μ, 5.62μ, 5.97μ, and 6.51μ.

The above disulphide compound can also be obtained as follows:

A solution of 0.317 g of 3,3-dimethyl-4-thia-2,6-diazabicyclo[3.2.0]heptan-7-one in 3.0 ml of methylene chloride is treated with 0.254 g of iodine in 12.0 ml of benzene; hereupon a voluminous brown precipitate forms immediately. The mixture is periodically shaken for 10 minutes at room temperature and then filtered, and the filter residue is washed with benzene and pentane and suspended in 8.0 ml of acetonitrile. The suspension is treated with 2.0 ml of pyridine, whereupon a clear yellow solution is obtained, which is cooled to +10° C. and is treated dropwise with 0.4 ml of phenylacetic acid chloride, whilst stirring. The reaction mixture is left to stand for 20 minutes at room temperature and is then concentrated to a weight of 1.9 g under reduced pressure. The yellow syrupy residue is taken up in 50 ml of ethyl acetate and the solution is washed with 50 ml of water and then evaporated. The residue is crystallised from a mixture of methanol, methylene chloride and hexane. Bis-[cis-2-oxo-3β-(N-phenylacetyl-amino)-4β-azetidinyl]-disulphide melts at 152°–155° C. after recrystallisation from acetone and methylene chloride (analytical preparation: 156.5°–158.5° C.).

A solution of 0.35 g of bis-[cis-2-oxo-3β-(N-phenylacetylamino)-4β-azetidinyl]-disulphide in 16 ml of a 9:1 mixture of acetic acid and water is treated at about 5° C. with about 3.2 g of ethylene oxide and then with 3.5 g of zinc dust. The reaction mixture is stirred for 15 minutes at about 5° C. and for 30 minutes at room temperature and is then filtered. The filtered residue is rinsed with acetone and the filtrate is evaporated. The residue is taken up in about 150 ml of ethyl acetate and the solution is washed with 50 ml of a saturated aqueous sodium bicarbonate solution and with 100 ml of a saturated aqueous sodium chloride solution, dried and evaporated. The residue, together with a crude product obtained analagously from 0.58 g of bis-[cis-2-oxo-3β-(N-phenylacetyl-amino)-4β-azetidinyl]-disulphide, is chromatographed on 50 g of silica gel. Elution with a 19:1 mixture of ethyl acetate and acetone yields 4β-(2-hydroxyethylmercapto)-3β-(N-phenylacetyl-amino)-azetidin-2-one as a single product, which after crystallisation, from a mixture of acetone and diethyl ether melts at 141°-142° C.; $[\alpha]_D^{20} = +44° \pm 2°$ (c=0.571 in ethanol); thin layer chromatography (silica gel; development with iodine): Rf 0.45 (system: ethyl acetate/acetone 1:1); infrared absorption spectrum (in mineral oil): characteristic bands at 3.01μ, 5.68μ, 6.01μ, 6.43μ and 6.52μ.

A solution of 0.61 g of 4β-(2-hydroxyethylmercapto)-3β-(N-phenylacetyl-amino)-azetidin-2-one in 10 ml of tetrahydrofurane is treated dropwise, at 0° C., with 1.38 g of chloroformic acid 2,2,2-trichloroethyl ester in 5 ml of tetrahydrofurane, and then with 1.06 g of pyridine of 5 ml of tetrahydrofuran. The reaction mixture is stirred under a nitrogen atmosphere for 15 minutes at 0° C. and for 2 hours at room temperature and is then taken up in 150 ml of methylene chloride. The methylene chloride solution is washed with a saturated aqueous sodium chloride solution, dried and evaporated. The residue is chromatographed on a 50-fold amount of silica gel; 3β-(N-phenylacetyl-amino)-4β-[2-(2,2,2-trichlorethoxycarbonyloxy)-ethylmercapto]-azetidin-2-one is eluted with a 1:1 of methylene chloride and ethyl acetate. After crystallisation and one recrystallisation from diethyl ether, the product is obtained in the form of colourless needles, melting point 99°-101° C.; thin layer chromatogram (silica gel): Rf ~0.46 (system: ethyl acetate; development with iodine); $[\alpha]_D^{20} = 3° \pm 2°$ (c=0.518 in chloroform); infrared absorption spectrum (in methylene chloride): characteristic bands at 2.88μ, 5.58μ, 5.64μ, 5.92μ and 6.62μ.

A mixture of 1.0 g of 3β-(N-phenylacetyl-amino)-4β-[2-(2,2,2-trichloroethoxycarbonyloxy)-ethylmercapto]-azetidin-2-one and 3.0 g of glyoxylic acid tert.-butyl ester hydrate in 50 ml of benzene is boiled for 16 hours under reflux whilst separating off water and is then cooled, twice washed with 25 ml of distilled water at a time, dried over sodium sulphate and evaporated. α-Hydroxy-α-{2-oxo-3β-(N-phenylacetyl-amino)-4β-[2-(2,2,2-trichloroethoxycarbonyloxy-ethylmercapto]-1-azetidinyl}-acetic acid tert.-butyl ester is obtained and is used further without purification.

The crude α-hydroxy-α-{2-oxo-3β-(N-phenylacetyl-amino)-4β-[2-(2,2,2-trichloroethoxycarbonyloxy)-ethylmercapto]-1-azetidinyl}-acetic acid tert.-butyl ester obtainable according to the above process is dissolved in 20 ml of a 1:1 mixture of dioxane and tetrahydrofurane and treated dropwise, at −10° C., with 0.54 ml of pyridine in 2 ml of dioxane and 0.48 ml of thionyl chloride in 10 ml of a 1:1 mixture of dioxane and tetrahydrofurane. The reaction mixture is stirred for 30 minutes at −10° C. to −5° C. and for one hour under a nitrogen atmosphere, the precipitate is filtered off, and the filtrate containing the α-chloro-α-{2-oxo-3β-(N-phenylacetyl-amino)-4β-[2-(2,2,2-trichloroethoxycarbonyloxy)-ethylmercapto]-1-azetidinyl}-acetic acid tert.-butyl ester is evaporated; the product is used further in the crude state.

A solution of the crude α-chloro-α-{2-oxo-3β-(N-phenylacetyl-amino)-4β-[2-(2,2,2-trichloroethoxycarbonyloxy)ethylmercapto]-1-azetidinyl}-acetic acid tert.-butyl ester obtainable according to the above process, in 30 ml of a 1:1 mixture of dioxane and tetrahydrofurane, is treated with 1.15 g of triphenylphosphine and 0.35 ml of pyridine and warmed for 2 hours at 50° C. and then evaporated to dryness. The residue is chromatographed on 30 g of pure silica gel, and elution with a 1:1 mixture of toluene and ethyl acetate yields α-{2-oxo-3β-(N-phenylacetyl-amino)-4β-[2-(2,2,2-trichloroethoxycarbonyloxy)-ethylmercapto]-1-azetidinyl}-α-triphenylphosphoranylidene-acetic acid tert.-butyl ester, which is contaminated with a little triphenylphosphine oxide and can be purified by means of preparative thin layer chromatography (silica gel; development with iodine); Rf ~0.57 (system: toluene/acetone 1:1); infrared absorption spectrum (in methylene chloride): characteristic bands at 3.00μ, 3.42μ, 5.68μ, 5.97μ, 6.10μ and 6.65μ.

A mixture of 0.225 g of α-{2-oxo-3β-(N-phenylacetylamino)-4β-[2-(2,2,2-trichloroethoxycarbonyloxy)-ethylmercapto]-1-azetidinyl}-α-triphenylphosphoranylidene-acetic acid tert.-butyl ester in 10 ml of a 9:1 mixture of acetic acid and water is treated with 3.0 g of zinc dust and stirred for 45 minutes at 15° C. The mixture is filtered and the filtrate is evaporated; the residue is taken up in 50 ml of ethyl acetate and the solution is washed with 25 ml of a saturated aqueous sodium bicarbonate solution and twice with 25 ml at a time of a saturated aqueous sodium chloride solution, dried over sodium sulphate and evaporated. a-[4β-(2-Hydroxyethylmercapto)-2-oxo-3β-(N-phenylacetyl-amino)-1-azetidinyl]-α-triphenylphosphoranylidene-acetic acid tert.-butyl ester is thus obtained; thin layer chromatogram (silica gel: development with iodine): Rf ~0.24 (system: toluene/acetone, 1:1).

B. A solution of 10.0 g of 3-isopropyl-4-thia-2,6-diazabicyclo[3,2,0]heptan-7-one in 200 ml of a 1:1 mixture of acetic acid and water is treated dropwise, over the course of 15 minutes, with 436 ml of an 0.2 molar solution of iodine in ethanol, and after standing for one hour is evaporated at room temperature under reduced pressure. The residue, containing bis-(cis-3β-amino-2-oxo-4β-azetidinyl)-disulphide, is dried in a high vacuum and is used further without purification.

The crude product obtainable according to the above process is dissolved in 200 ml of a 1:1 mixture of tetrahydrofurane and water, treated with 8.4 ml of triethylamine and slowly added dropwise to a mixture, cooled to −10° C., of N-tert.-butoxycarbonyl-D-α-phenylglycine, 8.95 ml of triethylamine and 8.40 g of chloroformic acid isobutyl ester in 170 ml of tetrahydrofurane. After one hour at 0° C. and a further hour at room temperature, the reaction mixture is concentrated to half and taken up in 800 ml of ethyl acetate. The solution is twice washed with 200 ml at a time of a saturated aqueous sodium bicarbonate solution and twice with 200 ml at a time of a saturated aqueous sodium chloride solution, dried over sodium sulphate and evaporated. The residue is chromatographed on 500 g of silica gel. Bis-[cis-3β-(N-tert.-butoxycarbonyl-D-α-phenylglycyl)-amino-2-oxo-4β-azetidinyl]-disulphide is eluted with ethyl acetate. The amorphous product melts at 163°-166° C., with decomposition; $[\alpha]_D^{20} = +145° \pm 1°$ (c=0.930 in chloroform); thin layer chromatogram (silica gel; development with iodine vapour): Rf ~0.33 (system: ethyl acetate); ultraviolet absorption spectrum (in ethanol): $\lambda_{max}$=257 mμ (ε=2200); infrared absorption spectrum (in methylene chloride): characteristic bands at 2.90μ, 2.98μ, 3.34μ, 5.63μ, 5.90μ, 6.68μ, 7.29μ, 8.11μ, 8.58μ, and 9.53μ.

A solution of 5.63 g of bis-[cis-3β-(N-tert.-butoxycarbonyl-D-α-phenylglycyl)-amino-2-oxo-4β-azetidinyl]-disulphide in 190 ml of a 9:1 mixture of acetic acid and water is treated with about 60 g of ethylene oxide and 56 g of zinc dust and vigorously stirred for one hour at room temperature. The mixture is filtered, the filtrate is concentrated, the residue is taken up in ethyl acetate, and the solution is washed with a saturated aqueous sodium bicarbonate solution and a saturated aqueous sodium chloride solution, dried over sodium sulphate and evaporated. The residue is chromatographed on 150 g of silica gel; elution is carried out with ethyl acetate and 3β-(N-tert.-butoxycarbonyl-D-α-phenylglycyl)-amino-4β-(2-hydroxyethylthio)-azetidin-2-one is thus obtained, melting at 130°–131° C. after crystallisation from a mixture of acetone and diethyl ether; $[α]_D^{20} = -64° ± 2°$ (c=0.622 in ethanol); thin layer chromatogram (silica gel; development with iodine vapour): Rf ~0.47 (system: ethyl acetate/acetone 1:1); infrared absorption spectrum (in methylene chloride): characteristic bands at 2.90μ, 3.00μ, 3.25μ, 3.34μ, 5.61μ, 5.83μ, 5.91μ, 6.68μ, 7.29μ, 8.58μ, and 9.02μ.

A solution, cooled to 0° C., of 4.80 g of 3α-(N-tert.-butoxycarbonyl-D-α-phenylglycyl)-amino-4β-(2-hydroxyethylthio)-azetidin-2-one and 7.74 g of chloroformic acid 2,2,2-trichloroethyl ester in 100 ml of tetrahydrofurane is treated over the course of 10 minutes with a solution of 5.9 g of pyridine in 50 ml tetrahydrofurane and the whole is stirred for 15 minutes at 0° C. and for 30 minutes at room temperature, and is concentrated. The residue is taken up in 500 ml of methylene chloride, and the methylene chloride solution is twice washed with 100 ml of a saturated aqueous sodium chloride solution and evaporated. This residue is chromatographed over 300 ml of silica gel and elution with a 4:1 mixture of methylene chloride and ethyl acetate yields non-crystalline 3β-(N-tert.-butoxycarbonyl-D-α-phenylglycyl)-amino-4β-[2-(2,2,2-trichloroethoxycarbonyloxy)-ethylthio]-azetidin-2-one, thin layer chromatogram (silica gel; development with iodine vapour): Rf ~0.55 (system: ethyl acetate) and Rf ~0.19 (system: toluene/ethyl acetate 1:1). Infrared absorption spectrum (in methylene chloride): characteristic bands at 3.00μ, 3.35μ, 3.42μ, 5.61μ, 5.66μ, 5.85μ, 5.92μ, 6.75μ, 7.06μ, 8.14μ and 8.61μ.

A mixture of 13.5 g of glyoxylic acid tert.-butyl ester hydrate in 160 ml of toluene is dehydrated by distilling off about 80 ml of toluene and is added to 5.29 g of 3β-(N-tert.-butoxycarbonyl-D-α-phenylglycyl)-amino-4β-[2-(2,2,2-trichloroethoxycarbonyloxy-ethylthio]-azetidin-2-one, and the reaction mixture is warmed for 16 hours at 90° C. under a nitrogen atmosphere. After cooling, it is diluted with toluene to a volume of 150 ml, washed five times with 100 ml of water at a time, dried over sodium sulphate and evaporated. The residue contains α-{3β-(N-tert.-butoxycarbonyl-D-α-phenylglycyl)-amino-4β-[2-(2,2,2-trichloroethoxycarbonyloxy)-ethylthio]-2-oxo-azetidinyl}-α-hydroxy-acetic acid tert.-butyl ester and is used further without purification.

The oily product is dissolved in 100 ml of a 1:1 mixture of tetrahydrofurane and dioxane and is treated, at about −5° C., with 2.24 ml of pyridine and, over the course of 10 minutes, with 2.00 ml of thionyl chloride in a 1:1 mixture of tetrahydrofurane and dioxane. After standing for 30 minutes at −5° C., the cooling bath is removed; the mixture is further stirred for one hour at room temperature, filtered through a diatomaceous earth preparation and evaporated. The residue contains α-chloro-α-{3β-(N-tert.-butoxycarbonyl-D-α-phenylglycyl)-amino-4β-[2-(2,2,2-trichloroethoxycarbonyloxy)ethylthio]-2-oxo-1-azetinyl}-acetic acid tert.butyl ester and is used further without purification.

The above crude product is dissolved in 100 ml of a 1:1 mixture of tetrahydrofurane and dioxane, 4.86 g of triphenylphosphine and 0.75 ml of pyridine are added, and the whole is warmed for 10 hours at 50° C. under a nitrogen atmosphere. The dark red solution is concentrated, the residue is taken up in methylene chloride, and the mixture is twice washed with 100 ml of water and then evaporated. The residue is chromatographed on 200 g of silica gel, α-{3β-(N-tert.-butoxycarbonyl-D-α-phenylglycyl)-amino-4β-[2-(2,2,2-trichloroethoxycarbonyloxy)-ethylthio]-2-oxo-1-azetidinyl}-α-triphenylphosphoranylidene-acetic acid tert.-butyl ester being eluted with a 1:1 mixture of toluene and ethyl acetate; thin layer chromatogram (silica gel; development with iodine vapour): Rf ~0.25 (system: toluene-/ethyl acetate, 1:1); infrared absorption spectrum (in methylene chloride): characteristic bands at 3.00μ, 3.44μ, 5.67μ, 5.86μ, 5.92μ, 6.14μ, and 6.76μ.

A solution of 1.74 g of α-{3β-(N-tert.-butoxycarbonyl-D-α-phenylglycyl)-amino-4β-[2-(2,2,2-trichloroethoxycarbonyloxy-ethylthio]-2-oxo-1-azetidinyl}-α-triphenylphosphoranylidene-acetic acid tert.-butyl ester in 65 ml of a 9:1 mixture of acetic acid and water is treated with 12 g of zinc dust and the mixture is stirred for one hour at room temperature. It is filtered through a diatomaceous earth preparation, the filtrate is evaporated, and the residue is taken up in 500 ml of ethyl acetate. The solution is twice washed with 100 ml of a saturated aqueous sodium bicarbonate solution and with 100 ml of a saturated aqueous sodium chloride solution and the organic phase is dried over sodium sulphate and evaporated. α-[3α-(N-Tert.-butoxycarbonyl-D-α-phenylglycyl)-amino-4α-(2-hydroxyethylthio)-2-oxo-1-azetidinyl]-α-(triphenylphosphoranylidene)-acetic acid tert.-butyl ester is thus obtained, thin layer chromatogram (silica gel; development with iodine vapour): Rf ~0.29 (system: toluene/acetone, 3:2): infrared absorption spectrum (in methylene chloride): characteristic bands at 3.00μ, 3.42μ, 5.68μ, 5.86μ, 5.93μ, 6.16μ, 6.75μ and 8.75μ.

EXAMPLE 38

Capsules containing 0.250 g of 7β-(D-α-phenylglycyl-amino-ceph-3-em-4-carboxylic acid are manufactured as follows:

Composition (for 100,000 capsules)

7β-(D-α-phenylglycyl)-amino-ceph-3-em-4-carboxylic acid: 25,000 g
Wheat starch: 2,500 g
Magnesium stearate: 1,000 g The 7β-(D-α-phenylglycyl)-amino-ceph-3-em-4-carboxylic acid, the wheat starch and the magnesium stearate are well mixed with one another and filled into No. 1 capsules.

EXAMPLE 39

Capsules containing 0.5 g of 7β-(D-α-phenylglycyl)-amino-ceph-3-em-4-carboxylic acid are prepared as follows:

Ingredients (for 2000 capsules)

7β-(D-α-phenylglycyl)-amino-ceph-3-em-4-carboxylic acid: 1000.00 g
Polyvinylpyrrolidone: 15.00 g
Corn starch: 115.00 g Magnesium stearate: 20.00 g The 7β-(D-α-phenylglycyl)-amino-ceph-3-em-4-carboxylic acid is moistened with 300 ml of a solution of the polyvinylpyrrolidone in 95% ethanol. The mixture is pressed through a sieve with 3-mm openings; the granulate is dried under reduced pressure at 40°–50°, broken on a screen of 0.88-mm openings and mixed with the corn starch and the magnesium stearate. The mixture is filled into hard gelatin capsules (No. 0).

We claim:

1. A compound selected from the group consisting of 7β-amino-ceph-3-em-4-carboxylic acid compounds of the formula:

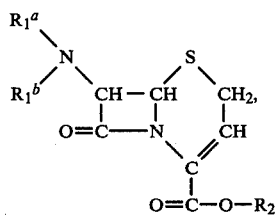

wherein $R_1^a$ and $R_1^b$ are hydrogen, and $R_2$ is a member selected from the group consisting of hydrogen, 2,2,2-trichloroethyl, 2-chloroethyl, 2-bromoethyl, 2-iodoethyl, phenacyl, 3- or 4-methoxybenzyl, 3,5-dimethoxybenzyl, 2-nitrobenzyl, 4,5-dimethoxy-2-nitrobenzyl, tert.-butyl, tert.-pentyl, benzhydryl, 4,4'-dimethoxybenzhydryl, 2-(4-biphenyl)-2-propyl, 2-furyl, adamantyl, 2-tetrahydrofuryl, 2-tetrahydropyranyl, 2,3-dihydro-2-pyranyl, 4-nitrophenyl, 2,4-dinitrophenyl, 4-nitrobenzyl, trichlorophenyl, pentachlorophenyl, phthaliminomethyl, succinyliminomethyl, trityl, bis-(4-methoxyphenyloxy)-methyl, benzyl, and lower alkanoyloxymethyl, and alkali metal salts, alkali earth metal salts, or an ammonium salt formed with ammonia, a lower alkylamine, hydroxylower alkylamine, lower alkyleneamine, cycloalkylamine, pyridine, collidine, or quinoline.

2. A compound according to claim 1 selected from the group consisting of 7β-amino-ceph-3-em-4-carboxylic acid compounds of the formula I, wherein $R_1^a$ and $R_1^b$ are hydrogen, and $R_2$ is a member selected from the group consisting of hydrogen, tert.-butyl, 2,2,2-trichloroethyl, 2-iodoethyl, 2-bromoethyl, phenacyl, 4-nitrobenzyl, 4-methoxybenzyl, benzhydryl, 4,4'-dimethoxydiphenylmethyl, trityl, and bis-(4-methoxyphenyloxy)-methyl, and an alkali metal salt, alkali earth metal salt, or an ammonium salt thereof formed with ammonia or a lower alkylamine.

3. A compound according to claim 1 being 7β-amino-ceph-3-em-4-carboxylic acid, and pharmaceutically acceptable salts of such compound.

4. A compound according to claim 1 being 7β-amino-ceph-3-em-4-carboxylic acid diphenylmethyl ester, and pharmaceutically acceptable salts of such compound.

* * * * *